United States Patent [19]

Sunagawa et al.

[11] Patent Number: 5,134,231
[45] Date of Patent: Jul. 28, 1992

[54] 3(1-HYDOXYETHYL)AZETIDINONE COMPOUNDS AND THEIR PRODUCTION

[75] Inventors: Makoto Sunagawa; Yoshihito Nozaki; Akira Sasaki; Haruki Matsumura, all of Osaka, Japan

[73] Assignee: Sumitomo Pharmaceuticals Company, Limited, Osaka, Japan

[21] Appl. No.: 642,531

[22] Filed: Jan. 17, 1991

Related U.S. Application Data

[63] Continuation of Ser. No. 338,544, Apr. 17, 1989, abandoned, which is a continuation of Ser. No. 946,017, Dec. 24, 1986, abandoned.

[30] Foreign Application Priority Data

Dec. 28, 1985 [JP] Japan .................................. 60-296999
Aug. 7, 1986 [JP] Japan .................................. 61-185958

[51] Int. Cl.$^5$ .................. C07D 205/08; C07D 407/06; C07D 307/52; C07D 309/30
[52] U.S. Cl. .................................. 540/200; 549/494; 549/291; 560/38; 560/39; 560/41; 560/170; 560/250; 560/253
[58] Field of Search ........................................ 540/200

[56] References Cited

U.S. PATENT DOCUMENTS 3,950,357  4/1976  Kahan et al. .................... 260/326.27
4,734,497  3/1988  Christensen .......................... 540/200
5,081,238  1/1992  Shibasaki .............................. 540/200

OTHER PUBLICATIONS

Johnston Journal of the American Chemical Society, vol. 100, pp. 313-315, 1987.
Shih Heterocycles, vol. 21, No. 1, pp. 29-40, 1984.

Primary Examiner—Mark L. Berch
Attorney, Agent, or Firm—Birch, Stewart, Kolasch & Birch

[57] ABSTRACT

An amino acid compound of the formula:

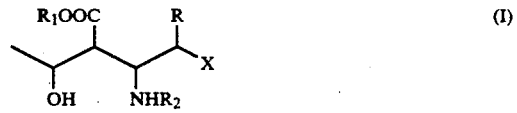

wherein R is a lower alkyl group, $R_1$ is a hydrogen atom or a protecting group for carboxyl, $R_2$ is a hydrogen atom, a protecting group for amino, an optionally substituted allyl group of the formula:

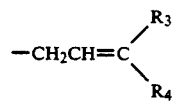

(wherein $R_3$ and $R_4$ are each a hydrogen atom, a lower alkyl group or an aryl group), a beta-hydroxyethyl group in which the hydroxyl group is optionally protected, a formylmethyl group in which the formyl group is optionally protected, a carboxymethyl group in which the carboxyl group is protected or a 2-furylmethyl group and X is an optionally protected carboxyl group, a hydroxymethyl group in which the hydroxyl group is optionally protected or a substituted mercaptomethyl group of the formula:

—CH$_2$SR$_5$ (wherein $R_5$ is an aryl group or an ar(lower)alkyl group), which is a useful intermediate in the synthesis of 1-alkylcarbapenem compounds.

5 Claims, No Drawings

3(1-HYDOXYETHYL)AZETIDINONE COMPOUNDS AND THEIR PRODUCTION

This application is a continuation of application Ser. No. 338,544, filed on Apr. 17, 1989, which is a continuation of application of application Ser. No. 946,017, filed on Dec. 24, 1986, both now abandoned.

The present invention relates to amino acid compounds and their production particularly, it relates to novel amino acid compounds useful as intermediates in the synthesis of 1-alkylcarbapenem compounds and their production.

The amino acid compounds of this invention are representable by the formula:

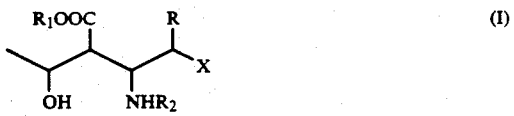

wherein R is a lower alkyl group, $R_1$ is a hydrogen atom or a protecting group for carboxyl, $R_2$ is a hydrogen atom, a protecting group for amino, an optionally substituted allyl group of the formula:

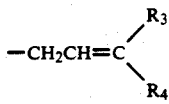

(wherein $R_3$ and $R_4$ are, the same or different, each a hydrogen atom, a lower alkyl group or an aryl group), a beta-hydroxyethyl group in which the hydroxyl group is optionally protected, a formylmethyl group in which the formyl group is optionally protected, a carboxymethyl group in which the carboxyl group is protected or a 2-furylmethyl group and X is an optionally protected carboxyl group, a hydroxymethyl group in which the hydroxyl group is optionally protected or a substituted mercaptomethyl group of the formula:

(wherein $R_5$ is an aryl group or an ar(lower)alkyl group).

Since the successful isolation of an antimicrobial substance "thienamycin" from the nature [U.S. Pat. No. 3,950,357; J.Am.Chem.Soc., 100, 313 (1978)], various carbapenem compounds have been synthesized. Among them, there are known some carbapenem compounds substituted at the 1-position, and 1-alkylcarbapenem compounds are particularly notable in exerting strong antimicrobial activity against various microorganisms with excellent stability in living bodies [Heterocycles, 21, 29 (1984)].

As a result of the extensive study, it has now been found that the amino acid compounds (I), which are novel, are valuable intermediates for the production of 1-alkylcarbapenem compounds.

Throughout this specification, particularly in the above formula (I), the term "lower" is generally intended to mean any group having not more than 8 carbon atoms, especially not more than 6 carbon atoms, more especially not more than 4 carbon atoms. Accordingly, for instance, the term "lower alkyl" includes methyl, ethyl, n-propyl, isopropyl, n-butyl, sec-butyl, t-butyl, etc. The term "lower alkoxy" includes methoxy, ethoxy, n-propoxy, isopropoxy, n-butoxy, sec-butoxy, t-butoxy, etc. The term "lower alkanoyl" covers acetyl, propionyl, butyryl, etc. Further, the term "halogen" is usually intended to mean chlorine, bromine, iodine and fluorine. Furthermore, the term "aryl" means normally an aromatic hydrocarbon group having not more than 20 carbon atoms such as phenyl, naphthyl or anthranyl. When the aryl group is substitued, the substituent(s) may be chosen from lower alkyl, lower alkoxy, nitro, amino, halogen, etc.

General protection of the functional groups such as carboxyl, amino, hydroxyl and formyl are disclosed in various textbooks such as "Protective Groups in Organic Synthesis" (1981) published by John Wiley & Sons, New York, U.S.A. and "New Experimental Chemistry" ("Shin-Jikken Kagaku Koza" in Japanese), Vol. 14 (1978) published by Maruzen, Tokyo, Japan as well as many literatures as cited in those textbooks. Conventional protecting groups as disclosed therein are ordinarily usable in this invention.

Specific examples of the protecting group for carboxyl are a lower alkyl group such as $C_1$-$C_4$ alkyl (e.g. methyl, ethyl, n-propyl, isopropyl, n-butyl, sec-butyl, t-butyl), a halogenated lower alkyl group such as $C_1$-$C_4$ alkyl substituted with one to three halogen atoms (e.g. 2-iodoethyl, 2,2,2-trichloroethyl), a lower alkoxymethyl group such as $C_1$-$C_4$ alkoxymethyl (e.g. methoxymethyl, ethoxymethyl, isobutoxymethyl), a lower alkoxycarbonyloxyethyl group such as $C_1$-$C_4$ alkoxycarbonyloxyethyl (e.g. 1-methoxycarbonyloxyethyl, 1-ethoxycarbonyloxyethyl), a lower alkanoyloxymethyl group such as $C_2$-$C_7$ alkanoyloxymethyl (e.g. acetoxymethyl, propionyloxymethyl, butyryloxymethyl, pivaloyloxymethyl), an optionally substituted lower alkenyl group such as optionally substituted $C_3$-$C_6$ allyl (e.g. allyl, 2-methylallyl, 3-methylally, cinnamyl), an optionally substituted arylmethyl group such as optionally substituted phenylmethyl (e.g. benzyl, p-methoxybenzyl, 2,4-dimethoxybenzyl, o-nitrobenzyl, p-nitrobenzyl, p-chlorobenzyl), an optionally substituted diarylmethyl group such as optionally substituted diphenylmethyl (e.g. diphenylmethyl, di-p-anisylmethyl), an optionally substituted aryl group such as optionally substituted phenyl (e.g. phenyl, p-nitrophenyl, p-chlorophenyl, 2,6-dimethylphenyl), etc.

Specific examples of the protecting group for amino are a lower alkoxycarbonyl group such as $C_1$-$C_5$ alkoxycarbonyl (e.g. t-butoxycarbonyl), a halogenated lower alkoxycarbonyl group such as $C_1$-$C_3$ alkoxycarbonyl substituted with one to three halogen atoms (e.g. 2-iodoethoxycarbonyl, 2,2,2-trichloroethoxycarbonyl), an optionally substituted arylmethoxycarbonyl group such as optionally substituted phenylmethoxycarbonyl (e.g. benzyloxycarbonyl, o-nitrobenzyloxycarbonyl, p-nitrobenzyloxycarbonyl, p-methoxybenzyloxycarbonyl), an optionally substituted arylmethyl group such as optionally substituted phenylmethyl group (e.g. benzyl, p-methoxybenzyl, 2,4-dimethoxybenzyl, o-nitrobenzyl, p-nitrobenzyl), an optionally substituted diarylmethyl group such as optionally substituted diphenylmethyl (e.g. diphenylmethyl, di-p-anisylmethyl), an alpha-lower alkyl-benzyl group such as alpha-$C_1$-$C_4$ alkylbenzyl(e.g. alpha-methylbenzyl, alpha-ethylbenzyl), a trityl group, a substituted aryl group such as substituted phenyl (e.g. p-methoxyphenyl, 2,4-dimethoxyphenyl, o-nitrophenyl, p-nitrophenyl, 2,4-dinitrophenyl), a tri(-lower)alkylsilyl group such as tri($C_1$-$C_4$)alkylsilyl (e.g.

trimethylsilyl, t-butyldimethylsilyl, t-butyldiphenylmethylsilyl), a substituted methyl group (e.g. methoxymethyl, 2-methoxyethoxymethyl, benzyloxymethyl, methylthiomethyl), a tetrahydropyranyl group, etc.

Specific examples of the protecting group for hydroxyl are a lower alkyl group such as $C_1-C_4$ alkyl (e.g. t-butyl), a substituted methyl group (e.g. methoxymethyl, benzyloxymethyl, 2-methoxyethoxymethyl, t-butoxymethyl, methylthiomethyl, 2,2,2-trichloroethoxymethyl), a tetrahydropyranyl group, a substituted ethyl group (e.g. 1-ethoxyethyl, 1-methyl-1-methoxyethyl, trichloroethyl), an optionally substituted monophenylmethyl, diphenylmethyl or triphenylmethyl group (e.g. benzyl, p-methoxybenzyl, o-nitrobenzyl, p-nitrobenzyl, p-chlorobenzyl, diphenylmethyl, triphenylmethyl), a substituted silyl group (e.g. trimethylsilyl, triethylsilyl, t-butyldimethylsilyl, t-butyldiphenylsilyl), a formyl group, a lower alkanoyl group such as $C_2-C_5$ alkanoyl (e.g. acetyl, isobutyroyl, pivaloyl), a halogenated lower alkanoyl group (e.g. dichloroacetyl, trichloroacetyl, trifluoroacetyl), an arylcarbonyl group (e.g. benzoyl, toluoyl, naphthoyl), a lower alkoxycarbonyl group such as $C_1-C_5$ alkoxycarbonyl (e.g. methoxycarbonyl, ethoxycarbonyl, isobutoxycarbonyl), a halogenated lower alkoxycarbonyl group such as $C_1-C_5$ alkoxycarbonyl substituted with one to three halogen atoms (e.g. 2-iodoethoxycarbonyl, ethoxycarbonyl, 2,2,2-trichloroethoxycarbonyl), a lower alkenyloxycarbonyl group such as $C_2-C_6$ alkenyloxycarbonyl (e.g. vinyloxycarbonyl, allyloxycarbonyl), an optionally substituted arylmethyloxycarbonyl group such as optionally substituted phenylmethyloxycarbonyl (e.g. benzyloxycarbonyl, p-methoxybenzyloxycarbonyl, 2,4-dimethoxybenzyloxycarbonyl, o-nitrobenzyloxycarbonyl, p-nitrobenzyloxycarbonyl), etc.

Examples of the protected formyl group are a di(-lower)alkoxymethyl group such as di($C_1-C_4$)alkoxymethyl (e.g. dimethoxymethyl, diethoxymethyl, di-n-propyloxymethyl), a di(halogenated lower alkoxy)methyl group (e.g. di(trichloroethoxy)methyl), a di(aryloxy)methyl group (e.g. di(phenyloxy)methyl), a di(aryl(lower)alkoxy)methyl group (e.g. dibenzyloxymethyl), a cyclic group of the formula:

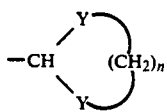

(wherein Y is an oxygen atom or a sulfur atom and n is an integer of 2 or 3, etc.

Among the amino acid compounds of the formula (I), preferred are those wherein R represents a methyl group. More preferred are those wherein R represents a methyl group, $R_2$ represents a benzyl group, a 2-propenyl group, a 2-furylmethyl group or a 2,2-dimethoxyethyl group.

The amino acid compound (I) can be produced from the corresponding acetylenamine compound of the formula:

wherein R, $R_1$, $R_2$ and X are each as defined above by reduction.

The reduction may be performed by a per se conventional reduction procedure such as catalytic hydrogenation using a catalyst (e.g. platinum, palladium, nickel), reduction with an alkali metal (e.g. lithium, sodium) in liquid ammonia or a lower alkylamine, reduction with a metal hydride such as aluminium hydride, an organic tin hydride (e.g. triethyltin hydride, tri-n-butyltin hydride, triphenyltin hydride) or a hydrosilane (e.g. trimethylsilane, triethylsilane, diethylsilane), reduction with an optionally substituted borane (e.g. diborane, 9-borabicyclo[3.3.1]nonane, dibenzoyloxyborane, monochloroborane, dichloroborane, catecholborane, dicyclohexylborane), reduction with a metal complex hydride (e.g. lithium aluminium hydride, sodium borohydride, sodium cyanoborohydride, lithium cyanoborohydride, sodium acetoxyborohydride), etc. The reduction may be accomplished in a single stage or two stages; in the at different stages.

Among various reduction procedures as above, the most preferred are the following two:

Procedure A:

The acetylenamine compound (II) is treated with a reducing agent (e.g. sodium cyanoborohydride, sodium borohydride, sodium acetoxyborohydride) in an inert solvent (e.g. acetic acid, propionic acid, ethanol, methanol) in the presence of an acid such as a mineral acid (e.g. hydrochloric acid, sulfuric acid) or a carboxylic acid (e.g. acetic acid, propionic acid, tartaric acid, oxalic acid) to give the amino acid compound (I). The reducing agent is usually employed in an amount of 2 to 5 equivalents to the acetylenamine compound (II). The treatment is normally effected at a temperature of about −40° C. to 80° C., although a lower temperature or a higher temperature may be adopted for suppressing or promoting the progress of the reduction. It is particularly preferred that the treatment is effected with sodium cyanoborohydride ($NaBH_3CN$) or sodium borohydride ($NaBH_4$) in the presence of acetic acid or propionic acid.

Procedure B:

The acetylenamine compound (II) is treated first with an optionally substituted borane and then with a reducing agent, followed by solvolysis to give the amino acid compound (I).

As the optionally substituted borane, there may be used diborane, 9-borabicyclo[3.3.1]nonane, dibenzoyloxyborane, monochloroborane, dichloroborane, catecholborane or the like, preferably catecholborane or the like. The amount of the optionally substituted borane may be usually from 1 to 2.5 equivalents to the acetylenamine compound (II). Treatment with the optionally substituted borane is usually effected in an inert solvent such as an ether (e.g. tetrahydrofuran, diethyl ether, dioxane, diglyme), a halogenated hydrocarbon (e.g. chloroform, dichloromethane) or an aromatic hydrocarbon (e.g. benzene, toluene) at a temperature of −100° C. to room temperature.

The subsequent treatment with a reducing agent (e.g. sodium cyanoborohydride, sodium borohydride) is usually performed in an inert solvent (e.g. acetic acid, propionic acid, ether, tetrahydrofuran, chloroform) in the presence of an acid (e.g. acetic acid, propionic acid, oxalic acid, hydrochloric acid, sulfuric acid) at a temperature of about −40° to 80° C. The amount of the reducing agent may be normally about 1 to 3 equivalents to the acetylenamine compound (II).

The solvolysis of the reaction product may be accomplished in a solvent such as water or methanol in the presence of a base (e.g. sodium hydrogen carbonate, sodium carbonate, sodium hydroxide) at a temperature of about 0 to 40° C.

The amino acid compound (I) comprises four asymmetric carbon atoms and have many optical isomers and stereo isomers based thereon. All of those isomers and their mixtures are included in this invention.

According to Procedure A or B as illustrated above, there are predominantly produced four kinds of isomers, i.e. the isomers of the following formulas:

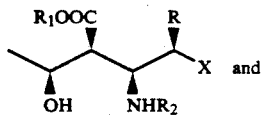

and

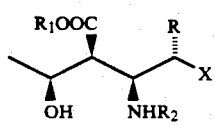

wherein R, $R_1$, $R_2$ and X are each as defined above and their respective enantiomers. Depedning upon the reaction conditions, the proportion of these isomers in the reaction mixture is varied. When appropriate reaction conditions are chosen, there is obtainable a reaction mixture comprising as the major products the isomer (Ia) and its enantiomer, said isomer (Ia) being derivable to the corresponding 18-alkylcarbapenem compound of the formula:

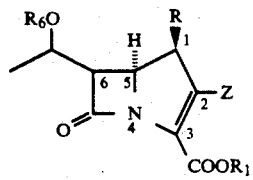

wherein R and $R_1$ are each as defined above, $R_6$ is a hydrogen atom or a protecting group for hydroxyl and Z is an organic group. Separation of each enantiomer may be accomplished by a procedure as hereinafter illustrated.

The amino acid compounds of the formula (I) are valuable intermediates for production of 1-alkylcarbapenem compounds and can be converted into the latter by various procedures, of which a typical one is illustratively shown in the following scheme:

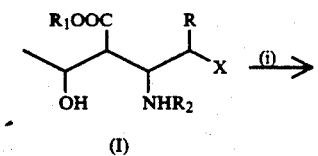

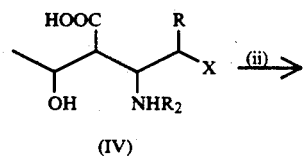

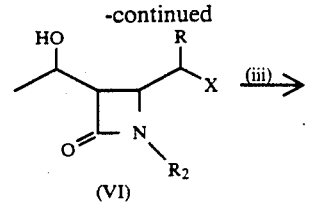

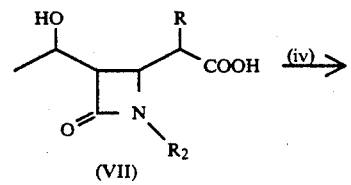

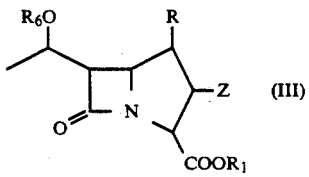

wherein R, $R_1$, $R_2$, $R_6$, X and Z are each as defined above.

Step (i):

The amino acid compound (I) is converted into the corresponding free acid (IV) by application of a per se conventional carboxyl-protecting group-elimination procedure thereto.

When the amino acid compound (I) wherein X is a protected carboxyl group is used as the starting material, it may be treated acccrding to the method as disclosed in Tetrahedron Letters, 21, 2783–2786 (1980) and 22, 913–916 (1981) to give the corresponding free acid as shown below:

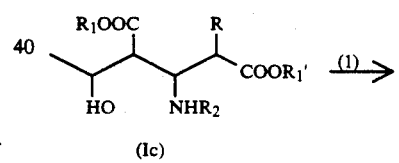

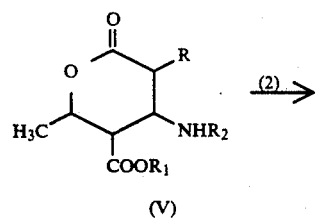

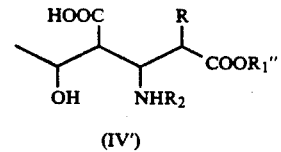

wherein R, $R_1$ and $R_2$ are each as defined above and $R_1$ and $R_1'''$ are each a protecting group for carboxyl.

The step (1) is concerned with lactonization of the compound (Ic) to the lactone (V). The lactonization may be accomplished by treatment of the compound (Ic) with a hydrogen halide (e.g. hydrogen chloride, hydrogen bromide) in an inert solvent such as a halogenated hydrocarbon (e.g. methylene chloride, chloroform, dichloroethane) or an ether (e.g. tetrahydrofuran, dioxane).

When the compound (Ic) is a mixture of the (Ia) type isomer and the (Ib) type isomer, the (Ia) type isomer is selectively converted into the compound (Va) as shown below, which can be derived to 1β-methyl or alkyl carbapenem compounds:

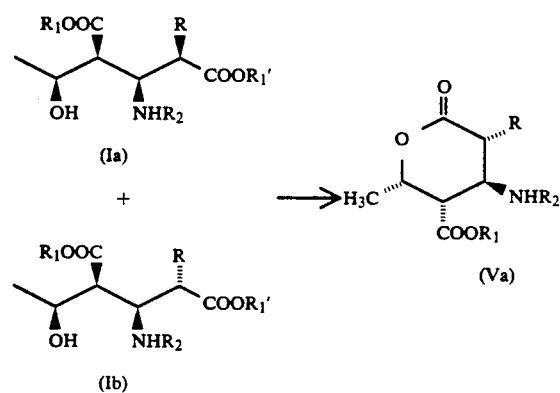

wherein R, $R_1$, $R_2$ and $R_1'$ are each as defined above.

In the step (2), the lactone (V) is converted into the free acid (IV'). This conversion may be accomplished in the manner as disclosed in the aforementioned literatures and will be hereinafter explained in detail. The lactone (V) involves a variety of stereo isomers, and the method as hereinafter explained is equally applicable to all of them, although the subsequent description will be made on the compound (Va) for the sake of convenience.

Method (a):

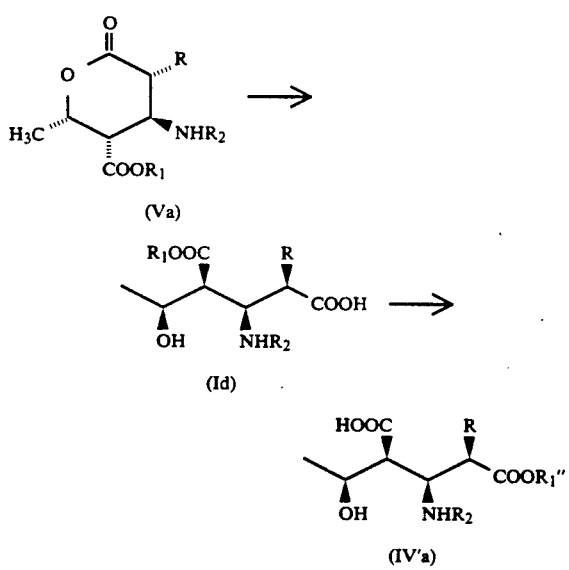

wherein R, $R_1$, $R_2$ and $R_1''$ are each as defined above.

The compound (Va) is subjected to seletive hydrolysis of the lactone ring with alkali to give the compound (Id), which is then subjected to protection of the free carboxyl group with a protecting group ($R_1''$) which is not influenced during the removal of the carboxyl-protecting group $R_1$, followed by removal of the latter ($R_1$) to give the compound (IV'a).

As the reagent in the selective hydrolysis, there may be used an aqueous solution of barium hydroxide, sodium hydroxide, potassium hydroxide, calcium hydroxide, tetrahydrobutylammonium hydroxide or the like, preferably an aqueous solution of barium hydroxide. The reaction medium is not limitative, and any one as conventionally used in alkali hydrolysis may be employed; preferred are tetrahydrofuran, acetone, methanol, pyridine, etc. and their mixtures with water. The reaction is favorably carried out at a temperature of 0° to 70° C., but a lower temperature or a higher perature may be adopted for suppression or promotion of the reaction. The carboxyl group-protection and the carboxyl group-elimination may be accomplished by per se conventional procedures, respectively.

Method (b):

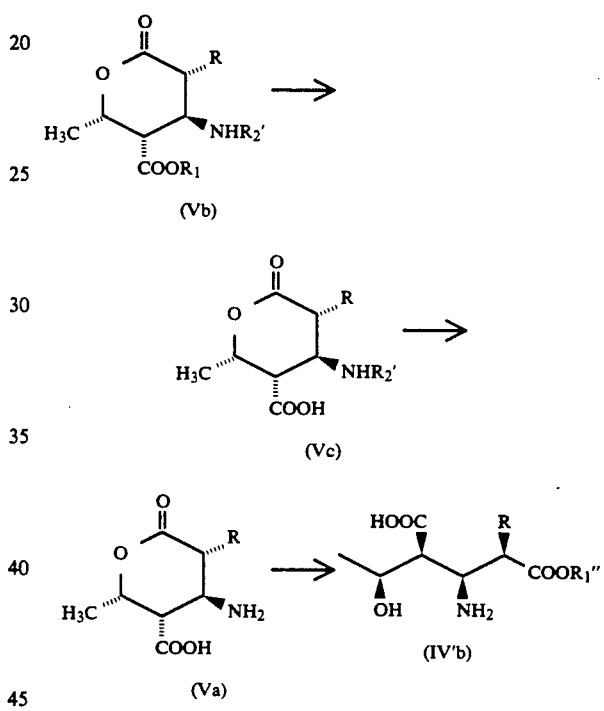

wherein R, $R_1$, $R_1''$ are each as defined above and $R_2'$ is a protecting group for amino.

The amino acid having a free amino group (IV'b) can be produced from the compound (Vb) by hydrolysis of the ester, elimination of the amino-protecting group and cleavage of the lactone ring. When, for instance, the carboxyl-protecting group is a lower alkyl group and the amino-protecting group is an arylmethyl group such as benzyl, the compound (Vb) is first treated with a mineral acid (e.g. hydrochloric acid), whereby selective hydrolysis takes place to give the compound (Vc). The compound (Vc) is then subjected to hydrogenolysis in the presence of a catalyst such as palladium hydroxide-carbon, whereby the amino-protecting group is removed to give the compound (Vd). Then, the compound (Vd) is subjected to alcoholysis by the use of an alcohol (e.g. benzyl alcohol), whereby the lactone ring is cleaved to give the compound (Iv'b).

Method (c):

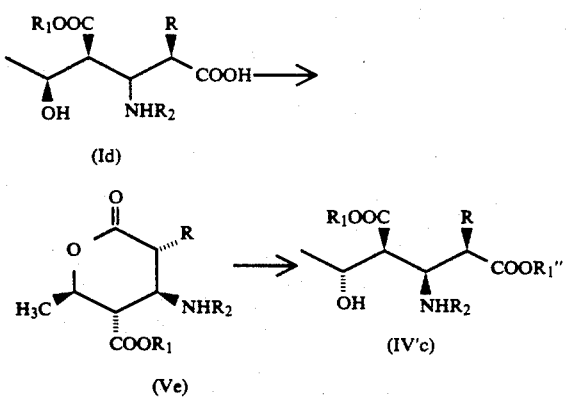

wherein R, $R_1$, $R_2$ and $R_1''$ are each as defined above.

The compound (IV'c) wherein the steric configuration of the hydroxyl group is inversed to that in the compound (IV'a) can be obtained from the amino acid compound (Id) by lactonization of the latter with diethyl azodicarboxylate and triphenylphosphine and conversion of the resultant compound (Ve) to the compound (IV'c) by application of Methods (a) and (b) as above.

In the lactonization, any auxiliary agent such as an organic base (e.g. triethylamine) may be used to accelerate production of the compound (Ve).

Alternatively, the compound (Ic) wherein X is a protected carboxyl group may be converted into the compound (Id) by selective hydrolysis with an alkali as set forth below:

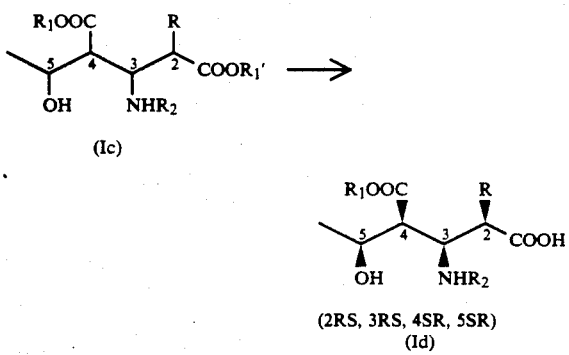

wherein R, $R_1$, $R_2$ and $R_1'$ are each as defined above.

As the reagent in the selective hydrolysis, there may be used an aqueous solution of barium hydroxide, sodium hydroxide, potassium hydroxide, calcium hydroxide, tetrahydrobutylammonium hydroxide or the like, among which an aqueous solution of barium hydroxide is the most preferred. The reaction medium may be any one as conventionally employed in conventional alkali hydrolysis, and there may be used, for instance, tetrahydrofuran, acetone, methanol, pyridine, etc. or their mixtures with water. The reaction is favorably carried out at a temperature of 0° to 70° C., but a lower temperature or a higher temperature may be adopted for suppression or acceleration of the reaction.

Step (ii):

The amino acid compound (IV) is subjected to dehydrative cyclization to give the azetidinone compound (VI). The dehydrative cyclization may be accomplished, for instance, by treatment of the amino acid compound (IV) with a dehydrating agent such as 2,2-dipyridyl disulfidetriphenylphospine or dicyclohexylcarbodiimide in the presence or absence of a base in an inert solvent [J.Am. Chem.Soc., 103, 2405-2406 (1981); Tetrahedron Letters, 21, 2783-2786 (1980); ibid., 22, 913-916 (1981)].

Step (iii):

With or without any previous protection of the hydroxyl group on the side chain at the 3-position by a per se conventional procedure, the azetidinone compound (VI) is converted into the corresponding carboxylic acid (VII). For this conversion, there may be adopted any appropriate procedure depending upon the kind of the group X. In case of X being a protected carboxyl group, the azetidinone compound (VI) may be subjected to hydrolysis, hydrogention, treatment with an acid or the like. In case of X being a protected hydroxymethyl group, the azetidinone compound (VI) may be subjected to removal of the hydroxyl-protecting group by a per se conventional procedure, and the thus recovered hydroxymethyl group is then oxidized, for instance, with chromic acid to give the compound (VII) [J.Am.Chem.Soc., 105, 1659-1660 (1983)]. In case of X being —$CH_2SR_5$, the azetidinone compound (VI) may be treated with an alkyl halide (e.g. methyl iodide) to convert —$CH_2SR_5$ into a halomethyl group, which is then changed to a hydroxymethyl group by a per se conventional procedure. The resultant hydroxymethyl group is then oxidized in the same manner as above to give the compound (VII) [Tetrahedron Letters, 5787 -5788 (1968)].

Step (iv):

The azetidinone compound (vII) wherein $R_2$ is a hydrogen atom is already known and used as the starting material for production of the 1-methyl or alkylcarbapenem compounds [Heterocycles, 21, 29-40 (1984); Tetrahedron Letters, 26, 587-590 (1985)]. When $R_2$ comprises any protecting group, an appropriate procedure for elimination of the protecting group such as hydrogenation, oxidative removal or treatment with an acid may be first applied to the azetidinone compound (VII), whereby the protecting group is eliminated.

When $R^2$ is a group of the formula:

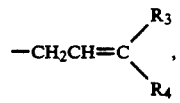

the azetidinone compound (VIII) may be converted into the azetidinone compound (X) as shown below [Japanese Patent Application No. 123117/1985]:

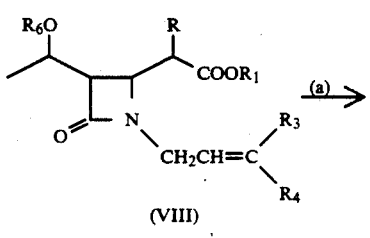

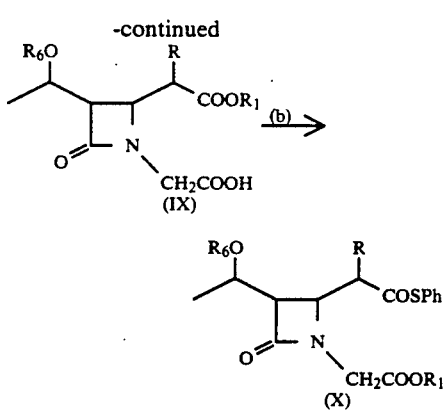

wherein R, $R_1$, $R_3$, $R_4$ and $R_6$ are each as defined above.

Namely, the compound (VIII) is first subjected to oxidation to give the compound (IX). The oxidation may be accomplished by a per se conventional procedure; for instance, the compound (VIII) is oxidized with ozone and then treated with an oxidizing agent (e.g. m-chloroperbenzoic acid), or treated with potassium permanganate in the presence or absence of a phase transfer catalyst such as a crown ether or a quaternary ammonium compound.

The thus produced compound (IX) is then subjected to protection of the carboxyl group, removal of the protecting group and acylation with thiophenol as set forth below, whereby the compound (X) is obtained:

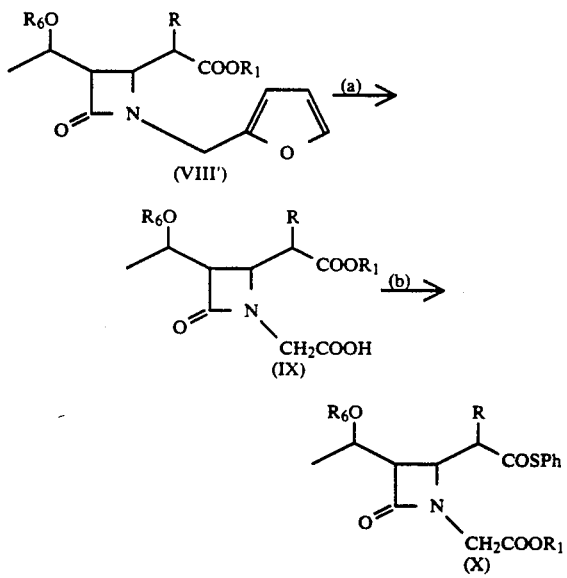

wherein R, $R_1$ and $R_6$ are each as defined above.

When $R_2$ is a 2-furylmethyl group, the compound (VIII') may be converted into the compound (X) through the compound (IX) in entirely the same manner as above.

When $R_2$ is a protected beta-hydroxyethyl group, the hydroxyl-protecting group is eliminated by a per se conventional procedure. The resulting beta-hydroxyethyl group is oxidized, for instance, with chromic acid to a carboxyl group. The thus produced compound, for instance, the compound (IX) may be then converted into the compound (X) in the same manner as above.

When $R_2$ is a protected formylmethyl group, the formyl-protecting group is eliminated by a per se conventional procedure. The resulting formylmethyl group is oxidized, for instance, with chromic acid to a carboxyl group. The thus produced compound, for instance, the compound (IX) may be then converted into the compound (X) in the same manner as above.

When $R_2$ is a protected carboxymethyl group, the carboxy-protecting group is eliminated by a per se conventional procedure. The resulting compound (IX) is then converted into the compound (X) in the same manner as above.

The compound (X) as above produced may be converted into the 1-methyl or alkylcarbapenem compound for instance, by the method as disclosed in Japanese Patent Application No. 290/480/85 as shown below:

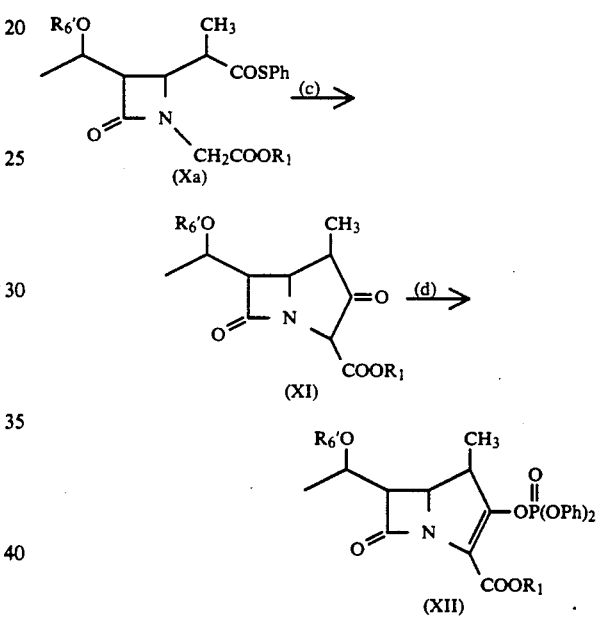

wherein $R_1$ is as defined above $R_6'$ is a protecting group for hydroxyl and Ph is a phenyl group.

In the above route, the conversion in the step (c) may be accomplished by treating the compound (Xa) with a base (e.g. sodium diisopropylamide, sodium hydride) in an inert solvent such as an ether (e.g. tetrahydrofuran), an aromatic hydrocarbon (e.g. toluene) and their mixtures. The subsequent conversion of the compound (XI) to the compound (XII) in the step (d) may be carried out by reacting the former with diphenylphosphoryl chloride in an inert solvent (e.g. acetonitrile) in the presence of a base (e.g. diisopropylethylamine).

The compound (XII) can be derived into various 1-methylcarbapenem compounds by known methods as already disclosed in many literatures.

As stated above, the amino acid compounds (I) have optical isomers due to the asymmetric carbon atoms present therein. All of these isomers as well as their racemic mixtures are included within the scope of this invention. Among them, preferred are the isomers (Ia), which are advantageous intermediates in the synthesis of the optically active 1β-methylcarbapenem compounds of the formula:

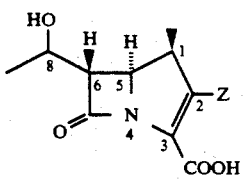

(IIIa)

wherein Z is as defined above.

The optically active 1β-methylcarbapenem compounds of the formula (IIIa) can be also produced by optical resolution of the compounds (VII) or of the carboxyl or amino group-containing compounds as the intermediates in the route from the amino acid compounds (I) to the compounds (VII). For instance, the optical resolution may be accomplished in the manner as set forth below.

A mixture of the (3S,4S) isomer and the (3R,4R) isomer of the compound (VII) is admixed with an optically active amine in an inert solvent to form a salt between the compound (VII) and the optically active amine, which is as such fractionally crystallized. Alternatively, said salt is once crystallized, and the collected crystals are subjected to fractional crystallization, whereby the optically active amine salt of the (3S,4S) isomer and the optically active amine salt of the (3R,4R) isomer are obtained.

Decomposition of the optically active amine salt of the (3S,4S) isomer or of the (3R,4R) isomer gives the (3S,4S) isomer or the (3R,4R) isomer.

As the optically active amine, there may be used alpha-phenethylamine, alpha-naphthylamine, norephedrine, cinchonine, cinchonidine, quinine, quinidine, 1-(2-naphthyl)ethylamine (NEA), brucine, 1,1-diphenyl-2-aminopropanol, 1-phenyl-2-(p-tolyl)ethylamine, etc. Among them, particularly preferred are cinchonine, cinchonidine, quinine, quinidine, etc.

As the inert solvent usable on production and/or decomposition of the optically active amine salt, there are exemplified hydrocarbons (e.g. pentane, hexane, cyclohexane), aromatic hydrocarbons (e.g. benzene, toluene, xylene), halogenated hydrocarbons (e.g. dichloromethane, chloroform, 1,2-dichloroethane), ethers (e.g. diethyl ether tetrahydrofuran, dioxane), alcohols (e.g. methanol, ethanol, isopropanol), nitriles (e.g. acetonitrile), ketones (e.g. acetone, methylethylketone), water, etc. Their mixtures are also usable. Among them, preferred are isopropanol, ethyl acetate, acetone and their mixtures.

Production of the salt is usually effected by dissolving a mixture of the isomers of the compound (VII) and the optically active amine in an inert solvent while heating up to the refluxing temperature of the solvent. The resultant solution is allowed to cool, if possible, gradually, whereby fractional crystallization takes place. Alternatively, said solution is cooled, and the precipitated crystals are collected by filtration; the collected crystals are subjected to fractional crystallization to precipitate one of the diastereomer salts. The precipitated diastereomer salt is collected, optionally followed by recrystallization to give the diastereomer salt of high purity.

Crystallization is usually performed within a range of 0° C. to room temperature, but a lower temperature range from −20° C. to room temperature or a higher temperature range up to 40° C. may be adopted.

The amount of the optically active amine may be appropriately controlled depending upon the mixing proportion of the isomers of the compound (VII). When, for instance, the proportion of the (3S,4S) isomer and the (3R,4R) isomer is 1 : 1, the optically active amine may be used in an amount of 0.5 to 1.2 mole, preferably of 1 to 1.1 mole, to 1 mole of the compound (VII).

The amount of an inert solvent usable for fractional crystallization is varied with the kind of the solvent. When, for instance, ethyl acetate is used as the solvent, its weight may be from 10 to 100 times, preferably from 20 to 40 times, that of the compound (VII).

The thus produced optically active amine salt of the desired isomer of the compound (VII) shows good filtrability. Further, it is of optically high purity. Therefore, the above explained process is advantageous from the industrial viewpoint.

Decomposition of the optically active amine salt as above obtained may be accomplished by treating said salt with an acid or an alkali in an inert solvent (e.g. water, methylisobutylketone, ethyl acetate, dichloroethane, 1,2dichloroethane). Application of conventional chemical and physical separation procedures to the reaction mixture gives the desired isomer of the compound (VII). As the acid usable for the decomposition, there may be favorably employed a mineral acid such as hydrochloric acid or sulfuric acid. Examples of the alkali usable are aqueous solutions of sodium hydroxide, potassium hydroxide, sodium carbonate, potassium carbonate, etc.

The optical resolution as above explained may be applied to any of the compounds (VII) wherein R, $R_2$ and $R_6$ have various meanings as above defined, but preferred are those of the formula (VII) wherein R is methyl, $R_2$ is a furylmethyl group, an optionally substituted monoarylmethyl group (e.g. benzyl, p-methoxybenzyl, 2,4-dimethoxybenzyl, o-nitrobenzyl, p-nitrobenzyl) or an optionally substituted diarylmethyl group (e.g. diphenylmethyl, di-p-anisylmethyl), especially furylmethyl, and $R_6$ is a hydrogen atom.

The compound (IIIa) has a 1-hydroxyethyl group at the 6-position, and the hydroxyl group in said 1-hydroxyethyl group attaches to the carbon atom at the 8-position. The compound (IIIa) wherein said hydroxyl group takes an S-configuration can be produced by using the compound (Ia) as such. The compound (IIIa) wherein said hydroxyl group takes an R-configuration can be obtained by inversion of the steric configuration of the hydroxyl group in any intermediate in the route from the compound (Ia) to the compound (VII). For inversion of the hydroxyl group, there may be adopted any conventional procedure such as the one using diethyl azodicarboxylate and triphenylphosphine [Tetrahedron Letters, 21, 2783-2786 (1980) and 22, 913-916 (1981)]or the one wherein the hydroxyl group is oxidized to an oxo group and the oxo group is stereospecifically reduced with a reducing agent such as potassium selectride [J.Am.Chem.Joc., 102, 6161-6163 (1980)].

The acetylenamine compound (II) as the starting material for production of the amino acid compound (I) can be manufactured by various processes, of which some typical examples are as follows:

Process [A]:

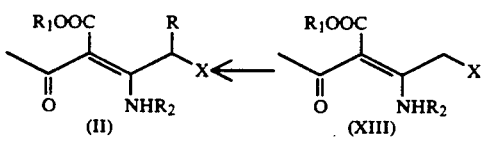

wherein $R_1$, $R_2$, X and R are each as defined above.

The acetylenamine compound (II) can be produced by reacting the acetylenamine compound (XIII) with an alkylating agent in the presence of a base in an inert solvent. Examples of the alkylating agent are lower alkyl halides (e.g. methyl iodide, ethyl iodide, n-butyl bromide), lower alkyl sulfonates (e.g. methyl tosylate, ethyl tosylate, methyl methanesulfonate, ethyl methanesulfonate, methyl trifluoromethanesulfonate). Examples of the base is alkali metal hydrides (e.g. sodium hydride, potassium hydride), alkali metal amides (e.g. sodium amide, lithium diisopropylamide, lithium bis(trimethylsilyl)amide), alkali metal alkoxides (e.g. sodium methoxide, sodium ethoxide, potassium methoxide, potassium t-butoxide), alkali metals (e.g. metallic sodium, metallic lithium), alkali metal carbonates (e.g. potassium carbonate, sodium carbonate), n-butyl lithium, sodium methylsulfinylmethide, etc. Examples of the inert solvent are aromatic hydrocarbons (e.g. benzene, toluene), ethers (e.g. diethyl ether, tetrahydrofuran, dioxane), ketones (e.g. acetone, methylisobutylketone), alcohols (e.g. methanol, ethanol, t-butanol), dimethylformamide, dimethylsulfoxide, hexamethylphosphoric amide (HMPT), etc.

The alkylating agent and the base are desired to be used respectively in sufficient amounts so that the reaction will proceed smoothly. The reaction may be effected at room temperature, but when desired, cooling or heating may be applied so as to suppress or accelerate the progress of the reaction. Post-treatment of the reaction mixture may be effected by a per se conventional procedure.

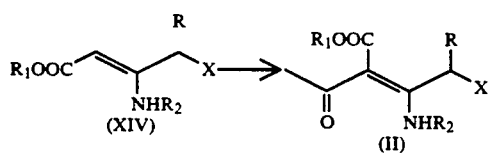

wherein R, $R_1$, $R_2$ and X are each as defined above.

The acetylenamine compound (II) can be produced by reacting the enamine compound (XIV) with an acetylating agent at the alpha-position to the ester group in an inert solvent. Examples of the acetylating agent are ketene, acetic anhydride, acetyl halides (e.g. acetyl chloride), etc. When acetic anhydride or an acetyl halide is used as the acetylating agent, the reaction is normally effected in the presence of a base (e.g. triethylamine, pyridine). Examples of the inert solvent are aromatic hydrocarbons (e.g. benzene, toluene), halogenated hydrocarbons (e.g. chloroform, dichloromethane, 1,2-dichloroethane), ethers (e.g. diethyl ether, tetrahydrofuran, dioxane), ketones (e.g. acetone, methylisobutylketcne), etc.

The acetylating agent and, when employed, the base are desired to be used respectively in sufficient amounts so that the reaction will proceed smoothly. The reaction may be effected normally at a temperature of $-10°$ to $95°$ C., but a lower temperature or a higher temperature may be adopted for suppressing or accelerating the reaction. Post-treatment of the reaction mixture may be effected by a per se conventional procedure.

The present invention will now be illustrated in greater detail with reference to the following Examples and Reference Examples, but it should be understood that these examples are given only for illustrative purposes and are not limiting the present invention.

In Examples and Reference Examples, the following abbreviations are used:
PNB: p-nitrobenzyl group
Bn: benzyl group
Ph: phenyl group
Me: methyl group
Et: ethyl group
tBu: t-butyl group
Tr: triphenylmethyl group
TBMS: t-butyldimethylsilyl group
BOM: benzyloxymethyl group
MOM: methoxymethyl group
MEM: 2-methoxyethoxymethyl group
MTM: methylthiomethyl group.

EXAMPLE 1

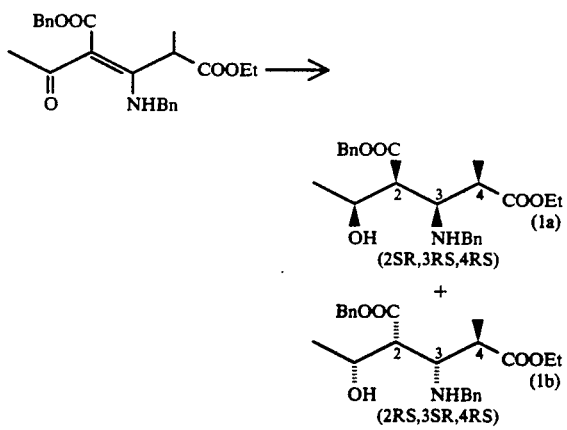

Ethyl benzyl 2-acetyl-3-benzylamino-4-methyl-2-pentenedioate (4.10 g; 10 mmole) was dissolved in dry tetrahydrofuran (40 ml), and catechol borane (1.56 g; 13 mmole) was dropwise added thereto at $-78°$ C., followed by stirring at the same temperature for 2 hours. The resulting mixture was returned to room temperature, and the solvent was removed by distillation under reduced pressure. To the residue, acetic acid (41 ml) was added, and sodium borohydride (757 mg; 20 mmole) was portionwise added thereto at 10° to 12° C., followed by stirring at the same temperature for 30 minutes and further at room temperature for 4 hours. Thereafter, acetic acid was distilled off at room temperature, and chloroform was added thereto. The organic layer was washed with a saturated sodium bicarbonate solution six times and then with an aqueous sodium chloride solution and dried over anhydrous sodium sulfate. Removal of the solvent under reduced pressure gave a mixture of ethyl benzyl (2SR,3RS,4RS)-2-[1(SR)-hydroxyethyl]-3-benzylamino-4-methylpentanedioate (1a) and ethyl benzyl (2RS,3SR,4RS)-2-(RS)-hydroxyethyl]-3-benzylamino-4-methylpentanedioate (1b) in a ratio of 98/2. Yield, 75 %.

IR (neat): 3335 (broad), 1720, 1445, 1152, 730, 690 (cm$^{-1}$).

NMR δ (CDCl$_3$):

(1a): 3.88 (ABq, 2H), 3.20 [t (J=4.9 Hz), 1H], 2.98 (m, 1H), 2.61 [dd (J=2.3 and 4.0 Hz), 1H]. (1b): 3.77 (ABq, 2H), 3.32 [dd (J=4.3 and 6.9 Hz), 1H], 2.86 (m, 1H), 2.58 [dd (J=2.6 and 4.3 Hz), 1H].

EXAMPLE 2

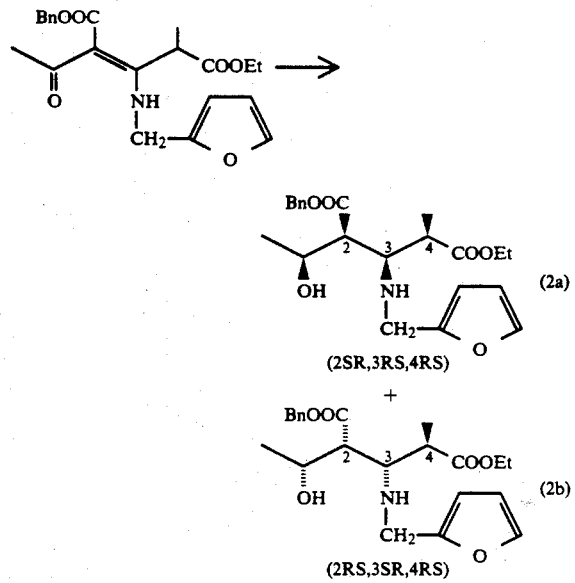

Ethyl benzyl 2-acetyl-3-furfurylamino-4-methyl-2-pentenedioate (400 mg; 1 mmole) was dissolved in dry tetrahydrofuran (4 ml), and catechol borane (156 mg; 1.3 mmole) was dropwise added thereto at −78° C., followed by stirring at the same temperature for 1 hour. The resulting mixture was returned to room temperature, and the solvent was removed by distillation under reduced pressure. To the residue, acetic acid (4.0 ml) was added, and sodium borohydride (76 mg; 2 mmole) was gradually added thereto at 10 to 12° C., followed by stirring at the same temperature for 30 minutes and further at room temperature for 3 hours. Thereafter, acetic acid was distilled off at room temperature, and chloroform was added thereto. The organic layer was washed with a saturated sodium bicarbonate solution six times and then with an aqueous sodium chloride solution and dried over anhydrous sodium sulfate. Removal of the solvent under reduced pressure gave a mixture of ethyl benzyl (2SR,3RS,4RS)-2-[1(SR)-hydroxyethyl]-3-furfurylamino-4-methylpentanedioate (2a) and ethyl benzyl (2RS,3SR,4RS)-2[1(RS)-hydroxyethyl]-3-furfurylamino-4-methylpentanedioate (2b) in a ratio of 97/3. Yield, 74 %.

IR (CHCl₃): 1723, 1452, 1373, 1260, 1160 (cm⁻¹).
NMR δ (CDCl₃)

(2a): 7.36 (m, 5H), 6.30 [dd (J=2.0 and 3.3 Hz), 1H], 6.20 (d (J=3.3 Hz), 1H], 5.12 (ABq, 2H), 4.09 [q (J=7.3 Hz), 2H], 4.01 [dq (J=2.3 and 6.6 Hz), 1H], 3.88 (ABq, 2H), 3.15 [dd (J=4.0 and 5.6 Hz), 1H], 2.90 (m, 1H), 2.59 [dd (J=2.3 and 3.6 Hz), 1H], 1.18– 1.26 (9H).

EXAMPLE 3

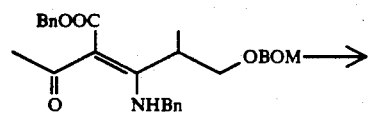

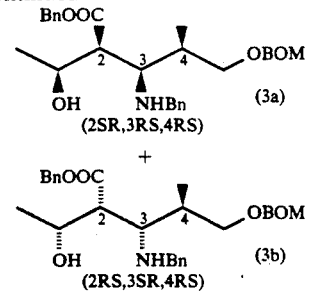

Benzyl 2-acetyl-3-benzylamino-4-methyl-5-benzyloxymethyloxy-2-pentenoate (23 mg; 0.047 mmole) was dissolved in propionic acid (0.2 ml), and sodium cyanoborohydride (6 mg; 0.095 mmole) was gradually added thereto at −20° to −25° C., followed by stirring at the same temperature for 6 hours. The solvent was removed under reduced pressure at room temperature, and the residue was dissolved in chloroform. The organic layer was washed with a saturated sodium bicarbonate solution three times and then with an aqueous sodium chloride solution two times and dried over anhydrous sodium sulfate. The solvent was removed by distillation under reduced pressure. The residue was purified by silica gel column chromatography to give a mixture of benzyl (2SR,3RS,4RS)-2-[1(SR)-hydroxyethyl]-3-benzylamino-4-methyl-5-benzyloxymethyloxypentanoate (3a) and benzyl (2RS,3SR,4RS)-2-[1(RS)-hydroxyethyl]-3-benzylamino-4-methyl-5-benzyloxymethyloxypentanoate (3b) in a ratio of 43. Yield, 74 %.

IR (neat): 3340, 1720, 1446, 1150, 1045, 728, 693 (cm⁻¹).

NMR δ (CDCl₃):

(3a): 7.32 (m, 15H), 5.12 (ABq, 2H), 4.66 (s, 2H), 4.57 (s, 2H), 4.06 [dq (J=2.3 and 6.6 Hz), 1H], 3.85 (ABq, 2H), 3.52 [dd (J=6.3 and 9.6 Hz), 1H], 3.43 [dd (J=5.9 and 9.9 Hz), 1H], 3.08 [t (J=4.6 Hz), 1H], 2.61 q (J=2.3 Hz), 1H], 2.21 (m, 1H), 1.20 [d (J=6.6 Hz), H], 1.01 (d (J=6.9 Hz), 3H].

(3b): 7.31 (m, 15H), 5.13 (s, 2H), 4.72 (s, H), 4.56 (s, 2H), 4.10 [dq (J=2.3 and 6.6 Hz), 1H], 3.83 (ABq, H), 3.54 (m, 2H), 3.17 [dd (J=3.6 and 5.3 Hz), 1H], 2.59 (m, 1H), 2.29 (m, 1H), 1.17 [d (J=6.6 Hz), 3H], 0.84 [d (J =7.3 Hz), 3H].

EXAMPLE 4

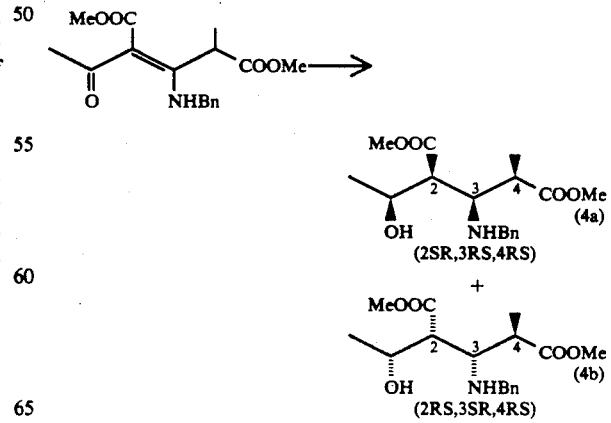

A solution of dimethyl 2-acetyl-3-benzylamino-4-methyl-2-pentenedioate (20 g; 62.6 mmole) in acetic acid (135 ml) was dropwise added to a solution of sodium cyanoborohydride (7.86 g; 125 mmole) in acetic acid (121 ml) at 10° to 12° C. in 20 minutes, and the resultant mixture was stirred at the same temperature for 2 hours. Acetic acid was removed under reduced pressure, and the residue was diluted with ethyl acetate and washed with a saturated sodium bicarbonate solution three times and then with an aqueous solution of sodium chloride one time. The reaction mixture was dried over anhydrous sodium sulfate, the solvent was removed under reduced pressure and the residue was purified by silica gel column chromatography to give a mixture of dimethyl (2SR,3RS,4RS)-2-[1(SR)-hydroxyethyl]-3-benzylamino-4-methylpentanedioate (4a) and dimethyl (2RS,3SR,4RS)-2-[1(RS)-hydroxyethyl]-3-benzylamino-4-methylpentanedioate (4b) in a ratio of 3/1 (calculated on the basis of the integral ratio in NMR). Yield, 70 %.

IR (neat): 3340, 1730, 1160, 1023, 735, 693 (cm⁻¹).

NMR δ (CDCl₃):

(4a): 3.14 [t (J=4.6 Hz), 1H], 2.57 [dd (J =2.3 and 4.0 Hz), 1H], 1.23 [d (J=6.6 Hz, 3H], 1.18 [d (J =6.9 Hz), 3H].

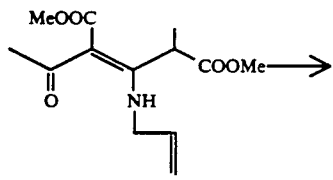

EXAMPLE 5

In the same manner as in Example 4 but using dimethyl 2-acetyl-3-allylamino-4-methyl-2-pentenedioate (830 mg; 3.08 mmole) and sodium cyanoborohydride (387 mg; 6.16 mmole), there was produced a mixture of dimethyl (2SR,3RS,4RS)-2-[1(SR)-hydroxyethyl]-3-allylamino-4-methylpentanedioate (5a) and dimethyl (2RS,3SR,4RS)-2-[1(RS)hydroxyethyl]-3-allylamino-4-methylpentanedioate (5b) in a ratio of 3.2/1 (calculated on the basis of the integral ratio in NMR). Yield, 69 %.

IR (neat): 3350, 1735, 1436, 1198, 1164 (cm⁻¹)

NMR δ (CDCl₃)

(5a): 3.69 (s, 3H), 3.67 (s, 3H), 3.54 [dd (J=5.6 and 13.5 Hz), 1H], 2.57 [dd (J=2.0 and 3.6 Hz), 1H], 1.23 [d (J=7.3 Hz), 3H], 1.18 [d (J=6.9 Hz), 3H].

EXAMPLE 6

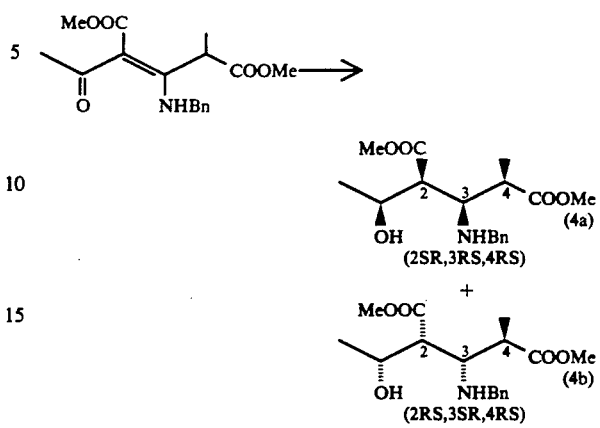

Dimethyl 2-acetyl-3-benzylamino-4-methyl-2-pentenedioate (32 mg; 0.1 mmole) was dissolved in dry tetrahydrofuran (0.1 ml), and a 0.55 N catechol borane solution in tetrahydrofuran (0.2 ml) was dropwise added thereto at −70° C. The resultant mixture was stirred at the same temperature for 2 hours, returned to room temperature and concentrated under reduced pressure. The residue was dissolved in acetic acid (0.1 ml), sodium cyanoborohydride (13 mg; 0.2 mmole) was added thereto at 10° to 12° C., and the resultant mixture was stirred at the same temperature for 1 hour and at room temperature for 1.5 hours. Acetic acid was removed at room temperature under reduced pressure, and the residue was dissolved in chloroform. The organic layer was washed with a saturated sodium bicarbonate solution six times and then with an aqueous solution of sodium chloride one time and dried over anhydrous sodium sulfate. Removal of the solvent under reduced pressure gave a mixture of dimethyl (2SR,3RS,4RS)-2-[1(SR)-hydroxyethyl]-3-benzylamino-4-methylpentanedioate (4a) and dimethyl (2RS,3SR,4RS)-2-[1(RS)-hydroxyethyl]-3-benzylamino-4-methylpentanedioate (4b) in a ratio of 94/6 (calculated on the basis of the integral ratio in NMR). Yield, 78 %.

The IR and NMR data obtained in this example were identical with those obtained in Example 4.

EXAMPLE 7

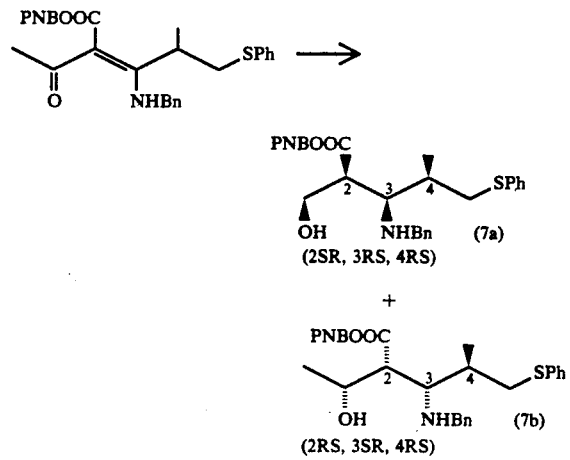

p-Nitrobenzyl 2-acetyl-3-benzylamino-4-methyl-5-phenylthio-2-pentenoate (101 mg; 0.2 mmole) was dissolved in acetic acid (0.2 ml), and sodium cyanoborohydride (15 mg; 0.24 mmole) was portionwise added thereto at 8° to 10° C., followed by stirring at the same temperature for 2 hours. After removal of acetic acid under reduced pressure, the reaction mixture was diluted with ethyl acetate. The organic layer was washed with a saturated sodium bicarbonate solution three times and then with an aqueous sodium chloride solution one time and dried over anhydrous sodium sulfate, followed by removal of the solvent under reduced pressure. The residue was purified by silica gel column chromatography to give a mixture of p-nitrobenzyl (2SR,3RS,4RS)-2-[1(SR)-hydroxyethyl]-3-benzylamino-4-methyl-5-phenylthiopentanoate (7a) and p-nitrobenzyl (2RS,3SR,4RS)-2-[1(RS)-hydroxyethyl]-3-benzylamino-4-methyl-5-phenylthiopentanoate (7b) in a ratio of 2/1. Yield, 75 %.

IR (neat): 3340, 1722, 1512, 1338, 1142, 728 (cm$^{-1}$).

NMR δ (CDCl$_3$)

(7a): 5.20 (s, 2H), 4.03 [dq (J=2.8 and 6.4 Hz), 1H], 3.76 (ABq, 2H), 3.11 [t (J=4.3 Hz), 1H], 3.05 [dd (J=8.5 and 12.8 Hz), 1H], 2.61 [dd (J=2.8 and 4.4 Hz), 1H], 2.53 [dd (J=8.6 and 12.8 Hz), 1H], 2.17 (m, 1H), 1.19 [d (J=6.3 Hz), 3H], 1.11 [d (J=6.9 Hz), 1H].

(7b): 5.20 (s, 2H), 4.02 [dq (J=2.6 and 6.6 Hz), 1H], 3.74 (ABq, 2H), 3.17 [dd (J=3.3 and 4.6 Hz), 1H], 2.90 [d (J=6.9 Hz), 2H], 2.53 [t (J=2.6 Hz), 1H], 2.26 (m, 1H), 1.15 [d (J=6.3 Hz), 3 H], 0.91 [d (J=7.3 Hz), 3H].

EXAMPLE 8

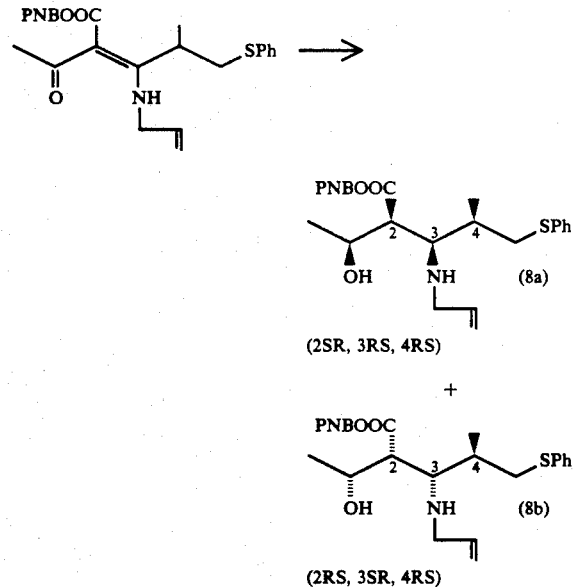

In the same manner as in Example 7 but using p-nitrobenzyl 2-acetyl-3-allylamino-4-methyl-5-phenylthio-2-pentenoate (92 mg; 0.2 mmole), there was produced a mixture of p-nitrobenzyl (2SR,3RS,4RS)-2-[1(SR)-hydroxyethyl]-3-allylamino-4-methyl-5-phenylthiopentanoate (8a) and p-nitrobenzyl (2RS,3SR,4RS)-2-[1(RS)-hydroxyethyl]-3-allylamino-4-methyl-5-phenylthiopentanoate (8b) in a ratio of 2/1.

IR (neat): 3360, 1730, 1521, 1342, 1152, 738 (cm$^{-1}$).

NMR δ (CDCl$_3$):

(8a): 5.81 (m, 1H), 5.22 (s, 2H), 5.08 (m, 2H), 4.04 [dq (J=2.6 and 6.6 Hz), 1H], 2.61 (dd (J=2.6 and 4.3 Hz), 1H], 2.54 [dd (J=8.6 and 12.5 Hz), 1H], 2.08 (m, 1H), 1.20 [d (J=6.3 Hz], 1.08 [d (J=6.8 Hz), 3H].

(8b): 5.83 (m, 1H), 5.21 (s, 2H), 5.13 (m, 4.09 [dq (J=2.6 and 6.6 Hz), 1H], 3.36 (dd (J=5.6 and 13.9 Hz), 1H], 3.14 [dd (J=3.3 and 5.3 Hz), 1H], 3.08 [dd (J=6.6 and 13.9 Hz), 1H], 2.90 [dd (J=3.3 and 7.3 Hz), 2H], 2.55 [t (J=3.3 Hz), 1H], 2.16 (m, 1H), 1.18 [d (J=6.3 Hz), 3H], 0.88 [d (J=7.3 Hz), 3H].

EXAMPLE 9

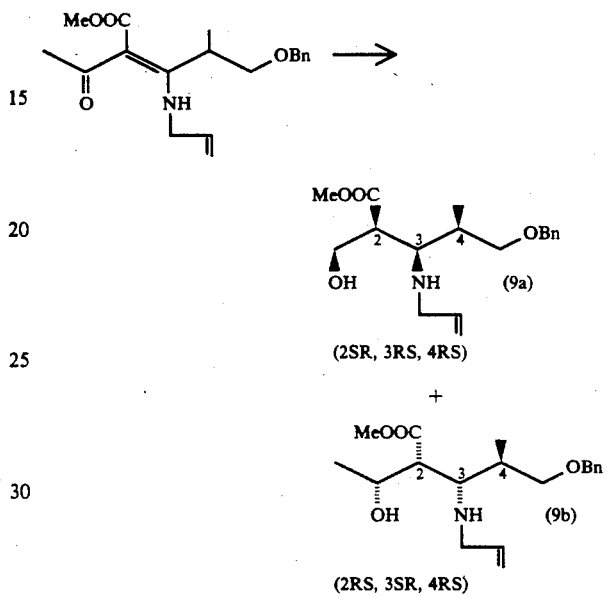

Methyl 2-acetyl-3-allylamino-4-methyl-5-benzyloxy-2-pentenoate (350 mg; 1.06 mmole) was dissolved in acetic acid (3.5 ml), and sodium cyanoborohydride (138 mg; 2.2 mmole) was portionwise added thereto, followed by stirring at 10° to 12° C. for 1 hour. After removal of acetic acid under reduced pressure, the reaction mixture was diluted with ethyl acetate. The organic layer was washed with a saturated sodium bicarbonate solution three times and then with an aqueous sodium chloride solution one time and dried over anhydrous sodium sulfate, followed by removal of the solvent under reduced pressure. The residue was purified by silica gel column chromatography to give a mixture of methyl (2SR,3RS,4RS)-2-[1(SR)-hydroxyethyl]-3-allylamino-4-methyl-5-benzyloxypentanoate (9a) and methyl (2RS,3SR,4RS)-2-[1(RS)-hydroxyethyl]-3-allylamino-4-methyl-5-benzyloxypentanoate (9b) in a ratio of 1.5/1 (calculated on the basis of the integral ratio in NMR).

IR (neat): 3349, 1725, 1450, 1158, 1086, 910, 732 (cm$^{-1}$)

NMR δ (CDCl$_3$):

(9a): 3.64 (s, 3H), 2.54 [dd (J=2.3 and 4.0 Hz), 1H], 1.20 [d (J=6.3 Hz), 3H], 1.00 [d (J=6.9 Hz), 3H].

(9b): 3.68 (s, 3H), 2.46 (m, 1H), 1.18 [d (J =6.6 Hz), 3H], 0.85 [d (J=6.9 Hz), 3H].

EXAMPLE 10 to 21

In the same manner as in Example 1, 3, 4 or 6, the amino acid compound (I) was produced as a mixture of the [1'SR,2SR,3RS,4RS] isomer (a) and the [1'RS,2RS,3SR,4RS] isomer (b) from the corresponding acetylenamine compound (II).

The reaction conditions, the yield and the ratio of the isomers (a) and (b) in the product are shown in Table 1.

TABLE 1

$$\underset{\underset{O}{\|}}{R_1OOC}\diagdown\diagup\diagdown\underset{NHR_2}{\diagup}X \longrightarrow \underset{\underset{OH}{|}}{R_1OOC}\overset{1'}{\diagdown}\overset{2}{\diagup}\overset{3}{\diagdown}\overset{4}{\diagup}X \text{ (OH NHR}_2\text{)} + \underset{\underset{OH}{|}}{R_1OOC}\overset{1'}{\diagdown}\overset{2}{\diagup}\overset{3}{\diagdown}\overset{4}{\diagup}X$$

(a) (1'SR,2SR,3RS,4RS)   (b) (1'RS,2RS,3SR,4RS)

| Example No. | Acetylenamine compound (II) R₁ | R₂ | X | Reaction condition*1 | Amino acid compound (I) Yield (%) | Ratio (a):(b)*2 | Physical data |
|---|---|---|---|---|---|---|---|
| 10 | Bn | Bn | COOEt | B | 78 | 1a:1b = 93:7 | Identical to those obtained in Example 1 |
| 11 | Bn | Bn | COOEt | A | 78 | 1a:1b = 7:3 | Identical to those obtained in Example 1 |
| 12 | Bn | —CH₂-furyl | COOEt | A | 65 | 2a:2b = 2:1 | Identical to those obtained in Example 2 |
| 13 | Bn | —CH₂CH(OMe)₂ | COOEt | A | 77 | 6a:6b = 2:1 | IR(neat)(cm⁻¹): 3340, 1715, 1443, 1376, 1245, 1160, 1127, 1060(broad), 955 NMRδ(CDCl₃): (6a): 4.36[dd(J=4.6 and 6.3 Hz), 1H], 2.82(m, 1H), 2.57[dd(J=2.3 and 4.3 Hz), 1H] (6b): 4.31[dd(J=4.6 and 6.3 Hz), 1H], 2.74(m, 1H), 2.60 [dd(J=3.0 and 4.6 Hz), 1H] |
| 14 | Et | Bn | COOEt | A | 74 | 10a:10b = 5:2 | IR(neat)(cm⁻¹): 3355, 1724, 1452, 1375, 1180, 738, 700 NMRδ(CDCl₃): (10a): 3.17[dd(J=4.0 and 5.0 Hz), 1H], 2.98(m, 1H), 2.55[dd(J=2.3 and 4.0 Hz), 1H] |
| 15 | Bn | Bn | CH₂OBOM | B | 48 | 3a:3b = 8:3 | Identical to those obtained in Example 3 |
| 16 | Bn | Bn | CH₂OTBMS | B | 55 | 11a:11b = 13:7 | IR(neat)(cm⁻¹): 3360, 1722, 1453, 1155, 1080, 735, 695 NMRδ(CDCl₃): (11a): 7.33(m, 10H), 5.15 (ABq, 2H), 4.06[dq(J= 2.3 and 6.3Hz), 1H], 3.87(ABq, 2H), 3.54 [dd(J=3.9 and 10.2Hz), 1H], 3.47[dd(J=3.9 and 10.2Hz), 1H], 3.10(br t, 1H), 2.61[dd(J=2.3 and 4.3Hz), 1H], 2.02(m, 1H), 1.22[d(J=6.6Hz), 3H], 1.03[d(J=6.9Hz), 3H] (11b): 7.31(m, 10H), 5.13 (s, 2H), 4.10[dq(J= 2.3 and 6.6Hz), 1H], 3.85(ABq, 2H), 3.64 [dd(J=5.3 and 10.2Hz), 1H], 3.47[dd(J=5.3 and 10.2Hz), 1H], 3.20[dd (J=3.3 and 5.3Hz), 1H], 2.60(m, 1H), 2.14(m, 1H), 1.24[d(J=6.3Hz), 3H], 0.80[d(J=6.9Hz), 3H] |
| 17 | Bn | Bn | CH₂OMEM | A | 65 | 12a:12b = 58:42 | IR(neat)(cm⁻¹): 3330, 1718, 1442, 1150, 1035, 730, 688 NMRδ(CDCl₃): (12a): 7.30(m, 10H), 5.14 (ABq, 2H), 4.63(ABq, 2H), 4.06[dd(J=2.3 and |

TABLE 1-continued

Scheme: R₁OOC-C(=O)-C(NHR₂)=CH-CH(CH₃)-X → (a) R₁OOC-CH(OH)-CH₂-CH(NHR₂)-CH(CH₃)-X (1'SR,2SR,3RS,4RS) + (b) R₁OOC-CH(OH)-CH₂-CH(NHR₂)-CH(CH₃)-X (1'RS,2RS,3SR,4RS)

| Example No. | Acetylenamine compound (II) $R_1$ | $R_2$ | X | Reaction condition*1 | Amino acid compound (I) Yield (%) | Ratio (a):(b)*2 | Physical data |
|---|---|---|---|---|---|---|---|
| | | | | | | | 6.3Hz), 1H], 3.86(ABq, 2H), 3.66(m, 2H), 3.53 (m, 2H), 3.45(m, 2H), 3.37(s, 3H), 3.08[t (J=4.6Hz), 1H], 2.60 [dd(J=2.3 and 4.6Hz), 1H], 2.20(m, 1H), 1.21 [d(J=6.3Hz), 3H], 1.00 [d(J=6.9Hz), 3H] (12b): 7.31(m, 10H), 5.13 (s, 2H), 4.68(s, 2H), 4.10[dq(J=2.4 and 6.3 Hz), 1H], 3.82(ABq, 2H), 3.64(m, 2H), 3.54(m, 4H), 3.36(s, 3H), 3.16 [dd(J=3.4 and 5.4Hz), 1H], 2.58[dd(J=2.4 and 3.4Hz), 1H], 2.29(m, 1H), 1.19[d(J=6.4Hz), 3H], 0.83[d(J=7.1Hz), 3H] |
| 18 | Bn | Bn | CH₂OMOM | B | 44 | 13a:13b = 7:3 | NMRδ(CDCl₃): (13a): 7.30(m, 10H), 5.14(s, 2H), 4.53(s, 2H), 4.06 (m, 1H), 3.85(ABq, 2H), 3.47[dd(J=5.9 and 9.6 Hz), 1H], 3.36[dd(J= 5.9 and 9.9Hz), 1H], 3.33(s, 3H), 3.08(m, 1H), 2.61[dd(J=2.3 and 4.6Hz), 1H], 2.21(m, 1H), 1.21[d(J=6.3 Hz), 3H], 1.01[d(J= 6.9Hz), 3H] (13b): 7.31(m, 10H), 5.13(s, 2H), 4.59(s, 2H), 4.11 [dq(J=2.3 and 6.3Hz), 1H], 3.83(ABq, 2H), 3.49(m, 2H), 3.33(s, 3H), 3.17[dd(J=3.3 and 5.3Hz), 1H], 2.57 [dd(J=2.3 and 3.3Hz), 1H], 2.29(m, 1H), 1.19 [d(J=6.3Hz), 3H], 0.83 [d(J=7.3Hz), 3H] |
| 19 | Bn | Bn | CH₂OMTM | A | 49 | 14a:14b = 58:42 | IR(neat)(cm⁻¹): 3330, 1722, 1447, 1152, 1063, 732, 693 NMRδ(CDCl₃): (14a): 7.31(m, 10H), 5.15(s, 2H), 4.50(ABq, 2H), 4.00(m, 1H), 3.87(ABq, 2H), 3.43[dd(J=6.3 and 9.3Hz), 1H], 3.34[dd (J=5.9 and 9.6Hz), 1H], 3.07(m, 1H), 2.63[dd (J=2.3 and 4.3Hz), 1H], 2.23(m, 1H), 2.11(s, 3H), 1.22[d(J=6.3Hz), 3H], 1.01[d(J=7.3Hz), 3H] (14b): 7.31(m, 10H), 5.14(s, 2H), 4.59(ABq, 2H), 4.11[dq(J=2.3 and 6.3 Hz), 1H], 3.82(ABq, 2H), 3.49(m, 2H), 3.15(m, 1H), 2.61(m, 1H), 2.29 (m, 1H), 2.10(s, 3H), 1.19[d(J=6.3Hz), 3H], 0.83[d(J=7.3Hz), 3H] |

TABLE 1-continued

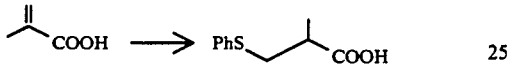

| | | | Reaction | Amino acid compound (I) | | |
|---|---|---|---|---|---|---|
| Example | Acetylenamine compound (II) | | condi- | Yield | Ratio | |
| No. | $R_1$ | $R_2$ | X | tion*1) | (%) | (a):(b)*2) | Physical data |
| 20 | Me | Bn | $CH_2OBn$ | A | 70 | 15a:15b = 3:2 | |
| 21 | Bn | —$CH_2COOBn$ | COOEt | A | 77 | 16a:16b = 7:3 | IR(neat)(cm$^{-1}$): 3380, 1756(sh), 1745(sH), 1723, 1452, 1375, 1150, 740, 698 |

Note:
*1)Reaction condition: A, same as in Example 4; B, same as in Example 6.
*2)The ratio was calculated on the basis of the integral ratio in NMR.

REFERENCE EXAMPLE 1-1

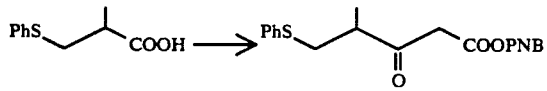

Methacrylic acid (6.88 g; 80 mmole) was dissolved in dry tetrahydrofuran (40 ml), and triethylamine (8.0 g; 80 mmole) and thiophenol (8.81 g; 80 mmole) were successively added thereto at room temperature, followed by stirring for 24 hours. Removal of the solvent under reduced pressure gave 2-methyl-3-phenylthiopropionic acid.

IR (neat): 1705, 1572, 1475, 1390, 1212, 1160 (cm$^{-1}$).

REFERENCE EXAMPLE 1-2

2-Methyl-3-phenylthiopropionic acid (4.60 g; 23.44 mmole) was dissolved in dry acetonitrile (20 ml), and 1,1-carbonyldiimidazole (4.56 g; 28.13 mmole) was added thereto with ice-cooling, and the resultant mixture was stirred at the same temperature for 30 minutes. The reaction mixture was dropwise added to a solution of malonic acid p-nitrobenzyl ester magnesium salt (17.53 g; 35 mmole) in dry acetonitrile (70 ml) at 50° C., and the resultant mixture was stirred at the same temperature for 30 minutes. After completion of the reaction, the reaction mixture was returned to room temperature and diluted with ethyl acetate. The organic layer was washed successively with 1N hydrochloric acid, water, a saturated sodium bicarbonate solution, water and an aqueous sodium chloride solution and dried over anhydrous sodium sulfate. The solvent was removed under reduced pressure, and the residue was purified by silica gel column chromatography to give p-nitrobenzyl 3-oxo-4-methyl-5-phenylthiopentanoate.

REFERENCE EXAMPLE 1-3

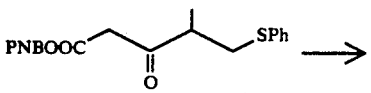

p-Nitrobenzyl 3-oxo-4-methyl-5-phenylthiopentanoate (1.12 g; 3 mmole) was dissolved in a mixture of methylene chloride (1 ml) and methanol (4 ml), and benzylamine (1.61 g; 15 mmole) and molecular sieve 3A (2 g) were added thereto. To the resultant mixture, a solution of acetyl chloride (785 mg; 10 mmole) in dry methanol (2 ml) was added and allowed to stand at room temperature for 2 days. The molecular sieve was removed by filtration, and the reaction mixture was diluted with ethyl acetate. The organic layer was washed successively with a saturated sodium bicarbonate solution, water and an aqueous sodium chloride solution, dried over anhydrous sodium sulfate and concentrated under reduced pressure. The residue was purified by silica gel column chromatography to give p-nitrobenzyl 3-benzylamino-4-methyl-5-phenylthio-2-pentenoate. pentenoate.

IR (neat): 1652, 1600, 1344, 1171, 733 (cm$^{-1}$).

REFERENCE EXAMPLE 1-4-(1)

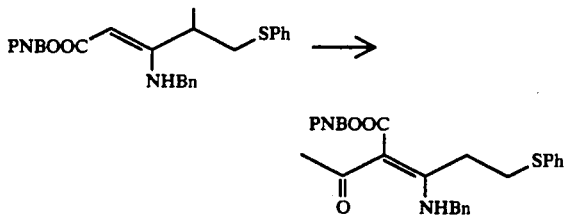

p-Nitrobenzyl 3-benzylamino-4-methyl-5-phenylthio-2-pentenoate (505 mg; 1 mmole) was dissolved in toluene (5 ml), and gaseous ketene was introduced therein at room temperature. After completion of the reaction, the solvent was removed under reduced pressure, and the residue was purified by silica gel column chromatography to give p-nitrobenzyl 2-acetyl-3-benzylamino-4-methyl-5-phenylthio-2-pentenoate.

IR (neat): 1705, 1583, 1519, 1341, 1270, 1092,737 (cm$^{-1}$).

REFERENCE EXAMPLE 1-4-(2)

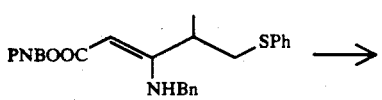

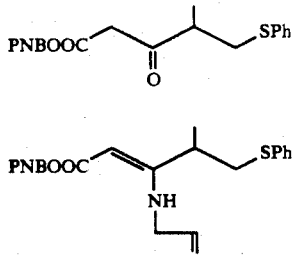

p-Nitrobenzyl 3-benzylamino-4-methyl-5-phenylthio-2-pentenoate (1.58 g; 3.51 mmole) was dissolved in tolune (5 ml), and trimethylamine (1.06 g; 10.5 mmole) was added thereto at 50° to 60° C. Acetyl chloride (630 mg; 8.0 mmole) was further added thereto all at once, and the resultant mixture was stirred for 10 minutes. Benzene (50 ml) was added to the reaction mixture, which was washed successively with a saturated sodium bicarbonate solution, water, dilute hydrochloric acid and an aqueous sodium chloride solution and dried over anhydrous magnesium sulfate. The solvent was removed under reduced pressure, and the residue was purified by silica gel column chromatography to give p-nitrobenzyl 2-acetyl-3-benzylamino-4-methyl-5-phenylthio-2-pentenoate.

REFERENCE EXAMPLE 1-5

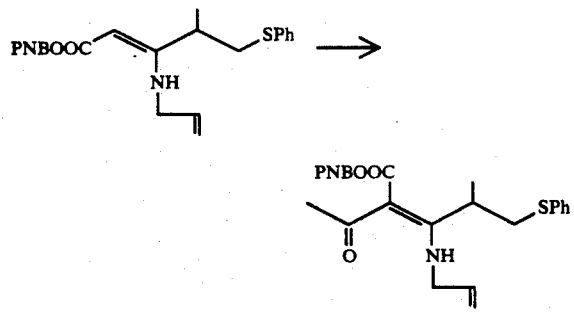

In the same manner as in Reference Example 1-3 but using allylamine (842 mg; 15 mmole), there was produced p-nitrobenzyl 3-allylamino-4-methyl-5-phenylthio-2-pentenoate.

IR (neat): 1650, 1596, 1342, 1163, 736 (cm$^{-1}$).

REFERENCE EXAMPLE 1-6

In the same manner as in Reference Example 1-4-(1) but using p-nitrobenzyl 3-allylamino-4-methyl-5-phenylthio-2-pentenoate (454 mg; 1 mmole), there was produced p-nitrobenzyl 2-acetyl-3-allylamino-4-methyl-5-phenylthio-2-pentenoate.

IR (neat): 1700, 1581, 1517, 1341, 1266, 733 (cm$^{-1}$).

REFERENCE EXAMPLE 2-1

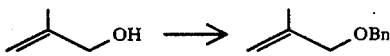

Under nitrogen stream, 50 % sodium hydride (5.28 g; 0.11 mole) was added to dry tetrahydrofuran (50 ml), and a solution of methallyl alcohol (7.2 g;0.1 mole) in dry tetrahydrofuran (20 ml) was portionwise added thereto with ice-cooling, followed by stirring for 30 minutes. A solution of benzyl bromide (17.1 g; 0.1 mole) in dry tetrahydrofuran (20 ml) was added thereto to quench the reaction. The reaction mixture was diluted with ethyl acetate and washed successively with 1N hydrochloric acid, water and an aqueous solution of sodium chloride and dried over anhydrous sodium sulfate. Removal of the solvent under reduced pressure gave 1-benzyloxy-2-methyl-2-propene.

IR (neat): 1650, 1490, 1442, 1090, 892 (cm$^{-1}$).

REFERENCE EXAMPLE 2-2

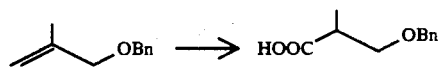

1-Benzyloxy-2-methyl-2-propene (8.1 g; 50 mmole) was dissolved in dry tetrahydrofuran (50 ml), and 1M boranetetrahydrofuran solution (25 ml; 25 mmole) was dropwise added thereto with ice-cooling, followed by stirring at room temperature for 1 hour. After addition of water (4 ml) and 3M sodium hydroxide solutoin (8.5 ml; 25.5 mmole), the reaction mixture was stirred at 40° C. for 5 minutes. Then, 35 % hydrogen peroxide solution (5.1 ml; 53 mmole) was added thereto, followed by stirring at the same temperature for 1.5 hours. The reaction mixture was returned to room temperature, a saturated sodium chloride solution (100 ml) was added thereto, and the resulting mixture was extracted with ether (150 ml×3). The ether extracts were combined together, dried over anhydrous magnesium sulfate and concentrated under reduced pressure to give crude 3-benzyloxy-2-methylpropanol (8.5 g). A portion (5.41 g; 30 mmole) of said crude product was dissolved in acetone (22 ml), and a Jones reagent (1.8 mmole/ml) (16.7 ml; 30 mmole) was dropwise added thereto with ice-cooling, followed by stirring for 3 hours. Insoluble materials were removed by filtration, and the filtrate was shaken with ice water (250 ml) and ethyl acetate (400 ml). The organic layer was extracted with a saturated sodium bicarbonate solution, and the extract was adjusted to pH 2 with conc. hydrochloric acid and extracted with ethyl acetate. The organic layer was dried over anhydrous sodium sulfate and concentrated under reduced pressure. The residue was purified by silica gel column chromatography to give 3-benzyloxy-2-methylpropionic acid.

IR (Nujol): 1695, 1455, 1070, 932, 706 (cm$^{-1}$).

Still, the hydroxyl group in methyl (S)-(+)-3-hydroxy-2-methylpropionate could be protected with a benzyl group by reacting it with benzyl bromide in the presence of silver oxide.

IR (neat): 1735, 1450, 1360, 1195, 1090, 735 (cm$^{-1}$).
NMR δ (CDCl$_3$): 7.32 (m, 5H), 4.52 (s, 2H), 3.70 (s, 3H), 3.66 [dd (J=2.7 and 9.2 Hz), 1H], 3.49 [dd (J=5.9 and 9.2 Hz), 1H], 2.79 (m, 1H), 1.18 [d (J=7.3 Hz), 3H].

REFERENCE EXAMPLE 2-3

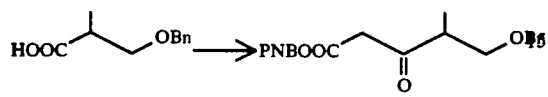

3-Benzyloxy-2-methylpropionic acid (3.0 g; 15.4 mmole) was dissolved in dry acetonitrile (20 ml), and 1,1'-carbonyldiimidazole (2.92 g; 18 mmole) was added thereto with ice-cooling, followed by stirring for 30 minutes. The resulting mixture was portionwise added to a solution of malonic acid p-nitrobenzyl ester magnesium salt (9.01 g; 18 mmole) in dry acetonitrile (40 ml) at 50° C., and the resultant mixture was heated under reflux for 3 hours. The reaction mixture was cooled to room temperature and diluted with ethyl acetate. The organic layer was washed successively with water, dilute hydrochloric acid, a saturated sodium bicarbonate solution and an aqueous sodium chloride solution and dried over anhydrous sodium sulfate. After removal of the solvent under reduced pressure, the residue was purified by silica gel column chromatography to give p-nitrobenzyl 3-oxo-5-benzyloxy-4-methylpentanoate.

IR (neat): 1720, 1683, 1576, 1490, 1316, 1065, 705 (cm$^{-1}$).

REFERENCE EXAMPLE 2-4

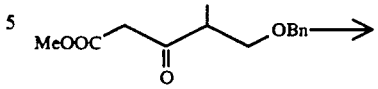

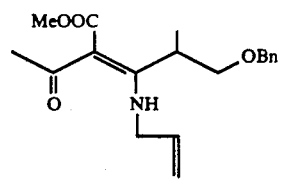

Sodium borohydride (1.89 g; 50 mmole) was added to methanol (20 ml), and the solution was heated under reflux for 10 minutes and then allowed to cool to room temperature. p-Nitrobenzyl 3-oxo-5-benzyloxy-4-methylpentanoate (3.7 g; 10 mmole) was dropwise added thereto, and the mixture was stirred at room temperature for 2 hours. The reaction mixture was diluted with ethyl acetate and washed with dilute hydrochloric acid and an aqueous solution of sodium chloride and dried over anhydrous sodium sulfate. After removal of the solvent under reduced pressure, the residue was purified by silica gel column chromatography to give methyl 3-oxo-5-benzyloxy-4-methylpentanoate.

IR (neat): 1742, 1713, 1622, 1448, 1305, 1090, 735 (cm$^{-1}$).

REFERENCE EXAMPLE 2-5

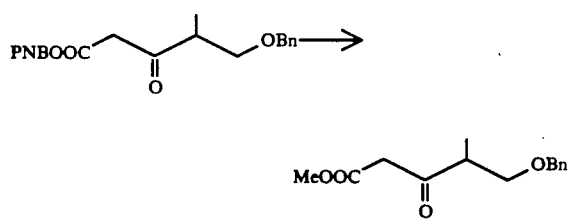

Methyl 3-oxo-4-methyl-5-benzyloxypentanoate (1.11 g; 4.43 mmole) was dissolved in dry methanol (5 ml), allylamine (1.26 g) and molecular sieve 3A (0.6 g) were added thereto and then a solution of acetyl chloride (1.04 g; 13.3 mmole) in dry methanol (2 ml) was added thereto with icecooling, followed by stirring at 40° C. for 12 hours. The molecular sieve was removed by filtration, and the filtrate was diluted with ethyl acetate. The reaction mixture was washed successively with a saturated sodium bicarbonate solution and an aqueous sodium chloride solution, dried over anhydrous sodium sulfate and concentrated under reduced pressure. The residue was dissolved in toluene (5 ml), and gaseous ketene was introduced therein at room temperature. After completion of the reaction, the solvent was removed under reduced pressure, and the residue was purified by silica gel column chromatography to give methyl 2-acetyl-3-allylamino-4-methyl-5-benzyloxy-2-pentenoate.

IR (neat): 1702, 1577, 1445, 1438, 1264, 1080, 736 (cm$^{-1}$).

REFERENCE EXAMPLE 3-1-(1)

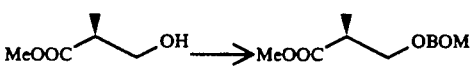

Methyl (S)-(+)-2-methyl-3-hydroxypropionate (2.0 g; 16.9 mmole) and diisopropylethylamine (2.2 g; 17.1 mmole) were dissolved in dry dichloromethane (2 ml), and benzyloxymethyl chloride (2.7 g; 17.3 mmole) was dropwise added thereto, followed by stirring for 1 hour. 1N Hydrochloric acid (10 ml) and ethyl acetate (20 ml) were added thereto, and the aqueous layer was extracted with ethyl acetate. The extract was combined with the organic layer, washed with a sodium bicarbonate solution and water and dried over anhydrous magnesium sulfate. After removal of the solvent under reduced pressure, the residue was purified by silica gel column chromatography to give methyl (S)-3-benzyloxymethyloxy-2-methylpropionate.

IR (neat): 1730, 1445, 1370, 1195, 1030 (cm$^{-1}$)
NMR δ (CDCl$_3$): 7.34 (s, 5H), 4.75 (s, 2H), 4.59 (s, 2H), 3.70 (s, 3H), 2.81 (m, 1H), 1.20 [d (J=7.0 Hz), 3H].

In the same manner as above but using methoxymethyl chloride or 2-methoxyethyl chloride in place of benzyloxymethyl chloride, there were produced the following methyl esters:

(1) 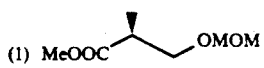

IR (neat): 1725, 1450, 1430, 1193, 1030, 910 (cm$^{-1}$).
NMR δ (CDCl$_3$): 4.61 (s, 2H), 3.70 (s, 2H), 3.65 (m, 2H), 3.34 (s, 3H), 2.79 (m, 1H), 1.19 [d (J=7.0 Hz), 3H].

(2) 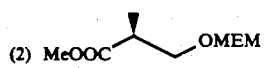

IR (neat): 1735, 1450, 1200, 1110, 1040 (cm$^{-1}$).
NMR δ (CDC13) 4.72 (s, 2H), 3.71 (s, 3H), 3.41 (s, 3H), 2.80 (m, 1H), 1.19 [d (J=7.3 Hz), 3H].

REFERENCE EXAMPLE 3-1-(2)

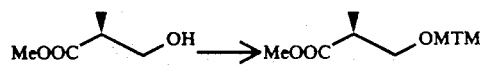

Methyl (S)-(+)-2-methyl-3-hydroxypropionate (2.36 g; 20 mmole) was dissolved in acetic anhydride (40 ml), and dry dimethylsulfoxide (40 ml) was added thereto, followed by stirring at room temperature for 5 days. The reaction mixture was diluted with water (500 ml) and extracted with a mixture of n-hexane and ethyl acetate (1:1). The organic layer was washed successively with water, a saturated sodium bicarbonate solution and water and dried over anhydrous sodium sulfate. After removal of the solvent under reduced pressure, the residue was purified by silica gel column methylpropionate.
IR (neat): 1730, 1450, 1432, 1160, 1042 (cm$^{-1}$).
NMR δ (CDC13) 1.20 [d (J=7.3 Hz), 3H], 2.13 (s, 3H), 2.76 (m, 1H), 3.5 - 3.8 (m, 2H), 3.71 (s, 3H), 4.63 (s, 2H).

REFERENCE EXAMPLE 3-1-(3)

Methyl (S)-(+)-2-methyl-3-hydroxypropionate (2.36 g; 20 mmole) was dissolved in dry dichloromethane (30 ml), conc. sulfuric acid (0.2 ml) was added thereto, and isobutene (23.5 g) was introduced into the resultant mixture kept at −60° to −70° C., followed by stirring at room temperature for 3 hours. The reaction mixture was sealed and stirred overnight, and unreacted isobutene was removed therefrom by distillation. The mixture was washed successively with water and a saturated sodium bicarbonate solution, dried over anhydrous sodium sulfate and concentrated under reduced pressure to give methyl (S)−3-t-butoxy-2-methylpropionate.
IR (neat): 1735, 1710 (sh), 1450, 1360, 1195, 1080, 1050 (cm$^{-1}$).
NMR δ (CDC13) 3.69 (s, 3H), 3.58 [dd (J=7.25 and 8.6 Hz), 1H], 3.35 [dd (J=6.2 and 8.6 Hz), 1H], 2.66 (m, 1H), 1.17 (s, 9H), 1.16 [d (J=7.0 Hz), 3H].

REFERENCE EXAMPLE 3-1-(4)

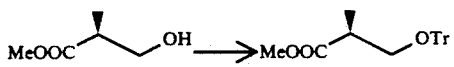

Methyl (S)-(+)-2-methyl-3-hydroxypropionate (1.18 g; 10 mmole), trityl chloride (3.1 g; 11.13 mmole) and N,N-dimethylaminopyridine (1.34 g; 11 mmole) were dissolved in dry dimethylformamide (10 ml), and the resultant mixture was stirred at room temperature overnight. Methanol (5 ml) was added thereto to decompose the unreacted trityl chloride, and the resultant mixture was stirred for 3 hours. Water (20 ml) was added to the reaction mixture, which was extracted with toluene (20 ml) three times. The extracts were combined together, washed with water, dried over anhydrous sodium sulfate and concentrated under reduced pressure. The residue was purified by silica gel column chromatography to give methyl (S)-3-trityloxy-2-methylpropionate.
IR (neat): 1725, 1450, 1370, 1195, 1080, 705 (cm$^{-1}$).
NMR 6 (CDC13): 7.43–7.22 (m, 15H), 3.70 (s, 3H), 3.28 [dd (J=7.1 and 8.75 Hz), 1H], 3.17 [dd (J=5.8 and 8.75 Hz), 1H], 2.73 (m, 1H), 1.15 [d (J=7.3 Hz), 3H].

REFERENCE EXAMPLE 3-1-(5)

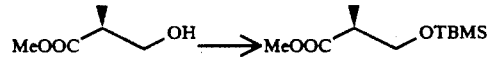

Methyl (S)-(+)-2-methyl-3-hydroxypropionate (1.0 g; 8.47 mmole) and imidazole (1.15 g; 16.9 mmole) were dissolved in dry dimethylfofmamide (10 ml), t-butyl dimethylchlorosilane (1.30 g; 8.62 mmole) was added thereto, and the resultant mixture was stirred at room temperature overnight. The reaction mixture was diluted with ethyl acetate (60 ml), washed with an aqueous sodium chloride solution (50 ml) three times and dried over anhydrous magnesium sulfate. After removal of the solvent, the residue was purified by silica gel column chromatography to give methyl (S)-3-t-butyldimethylsilyloxy-2-methylpropionate
IR (neat): 1740, 1460, 1250, 1195, 1090, 830, 770 (cm$^{-1}$).
NMR δ (CDC13): 3.78 [dd (J=6.9 and 9.6 Hz), 1H], 3.68 (s, 3H), 2.65 (m, 1H), 1.14 [d (J=6.9 Hz), 3H], 0.87 (s, 9H), 0.04 (s, 3H), 0.01 (s, 3H).

REFERENCE EXAMPLE 3-2-(1)

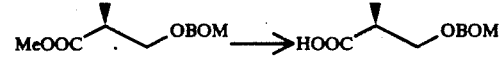

Methyl (S)-3-benzyloxymethyloxy-2-methylpropionate (1.20 g; 5 mmole) was dissolved in methanol (12 ml), and a 1N sodium hydroxide solution (5.5 ml) was added thereto with ice-cooling, followed by stirring at room temperature for overnight. The reaction mixture was diluted with water (30 ml) and washed with ether (20 ml) two times. The aqueous layer was acidified with 6N hydrochloric acid with ice-cooling and extracted with ethyl acetate (30 ml) three times. The extracts were combined together, washed with water and dried over anhydrous sodium sulfate and concentrated under reduced pressure to give (S)-3-benzyloxymethyloxy-2-methylpropionic acid.

IR (neat): 1705, 1445, 1370, 1100, 1035 (cm$^{-1}$).

NMR δ (CDCl3): 7.34 (s, 5H), 4.76 (s, 2H), 4.59 (s, 2H), 3.78 [dd (J=7.6 and 9.6 Hz), 1H], 3.68 [dd (J=5.3 and 9.6 Hz), 1H], 2.80 (m, 1H), 1.23 [d (J=7.25 Hz), 3H].

REFERENCE EXAMPLES 3-2-(2) to 3-2-(8)

In the same manner as in Reference Example 3-2-(1), the following carboxylic acids were produced from the corresponding methyl esters:

TABLE 2

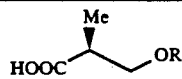

| Reference Example No. | R | IR (neat) (cm$^{-1}$) |
|---|---|---|
| 3-2-(2) | MOM | 1715, 1460, 1215, 1140, 1110, 1035, 917 |
| 3-2-(3) | MEM | 1735, 1710, 1455, 1195, 1115, 1040, 840 |
| 3-2-(4) | MTM | 1712, 1460, 1423, 1298, 1243, 1070, 1050 (sh) |
| 3-2-(5) | Bn | 1703, 1452, 1361, 1220, 1195 |
| 3-2-(6) | tBu | 1710, 1365, 1195, 1085, 1020, 880 |
| 3-2-(7) | Tr | 1702, 1490, 1445, 1220, 1070, 1015, 760, 740, 700 |
| 3-2-(8) | TBMS | 1710, 1490, 1450, 1220, 1070 |

REFERENCE EXAMPLE 3-3-(1)

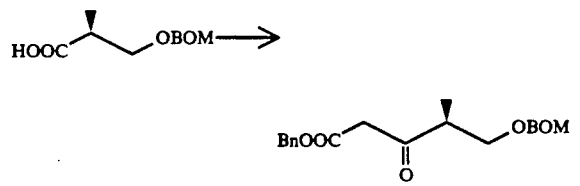

In the same manner as in Reference Example 1-2 but using (S)-3-benzyloxymethyloxy-2-methylpropionic acid (0.69 g; 3.075 mmole), 1,1′-carbonyldiimidazole (0.60 g; 3.675 mmole) and malonic acid monobenzyl ester magnesium salt (1.50 g; 3.675 mmole), there was produced benzyl (S)-3-oxo-4-methyl-5-benzyloxymethoxypentanoate.

IR (neat): 1735, 1710, 1445, 1035, 735, 690 (cm$^{-1}$).

NMR δ (CDCl3) 7.35 (s, 5H), 7.32 (s, 5H), 5.17 (s, 2H), 4.68 (s, 2H), 4.54 (s, 2H), 3.72 [dd (J=7.9 and 9.6 Hz), 1H], 3.61 (s, 2H), 2.96 (m, 1H), 1.10 [d (J=6.9 Hz), 3H].

REFERENCE EXAMPLES 3-3-(2) to 3-3-(8)

In the same manner as in Reference Example 3-3-(1), the following beta-keto esters were produced from the corresponding carboxylic acids:

TABLE 3

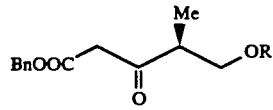

| Reference Example No. | R | IR (neat) (cm$^{-1}$) |
|---|---|---|
| 3-3-(2) | MOM | 1740, 1713, 1622, 1452, 1305, 1147, 1033 |
| 3-3-(3) | MEM | 1740, 1710, 1450, 1305, 1250, 1120, 1040, 845 |
| 3-3-(4) | MTM | 1737, 1708, 1620, 1448, 1300, 1145, 1060 |
| 3-3-(5) | Bn | 1735, 1710, 1618, 1447, 1300, 1140 |
| 3-3-(6) | tBu | 1745, 1715, 1450, 1360, 1195 |
| 3-3-(7) | Tr | 1750, 1710, 1620, 1490, 1450, 1302, 1153, 1055 |
| 3-3-(8) | TBMS | 1740, 1710, 1450, 1305, 1250, 1120, 1040, 845 |

REFERENCE EXAMPLE 3-4-(1)

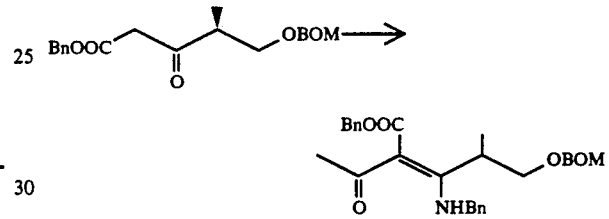

Benzyl (S)-3-oxo-4-methyl-5-benzyloxymethoxypentanoate (140 mg; 0.39 mmole) was dissolved in benzyl alcohol (0.9 ml), and molecular sieve 3A (0.2 g), benzylamine (50 mg; 0.47 mmole) and triethylamine hydrochloride (54 mg; 0.39 mmole) were added thereto, followed by stirring at 80° C. for 10 hours. The reaction mixture was diluted with chloroform (10 ml), and after removal of insoluble materials such as molecular sieve by filtration, the filtrate was washed with water. The organic layer was dried over anhydrous magnesium sulfate, followed by removal of the solvent under reduced pressure. Then, benzyl alcohol was removed under reduced pressure, and the residue was dissolved in dry toluene. Gaseous ketene was introduced therein at room temperature. After completion of the reaction, the reaction mixture was concentrated under reduced pressure. The residue was purified by silica gel column chromatography to give benzyl (R)-2-acetyl-3-benzylamino-4-methyl-5-benzyloxymethoxy-2-pentenoate.

IR (neat): 1700, 1580, 1448, 1352, 1270 (broad), 1097, 1033 (cm$^{-1}$).

REFERENCE EXAMPLES 3-4-(2) to 3-4-(8)

In the same manner as in Reference Example 3-4-(1), the following acetylenamines were produced from the corresponding beta-keto esters:

TABLE 4

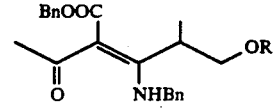

| Reference Example No. | R | Spectra data |
|---|---|---|
| 3-4-(2) | MOM | IR (CHCl3): 1708, 1586, 1450, 1358, 1265(sh), 1105, 1033(cm$^{-1}$) |

TABLE 4-continued

![structure: BnOOC-C(=O)-C(CH3)=C(NHBn)-CH(CH3)-CH2-OR]

| Reference Example No. | R | Spectra data |
|---|---|---|
| | | NMR δ (CDCl₃): 7.33(m, 10H), 5.20 s, 2H), 4.61[bd(J=5.0Hz), 2H], 4.49(ABq, 2H), 3.77[dd(J=6.9 and 9.6Hz), 1H], 3.62[dd(J=6.9 and 9.9Hz), 1H], 3.27(s, 3H), 3.24(m, 1H), 2.14(s, 3H), 1.22[d(J=7.3Hz), 3H] |
| 3-4-(3) | MEM | IR(neat): 1703, 1585, 1452, 1360, 1273(broad), 1105, 1037(cm⁻¹) |
| | | NMR δ (CDCl₃): 7.37(m, 10H), 5.20 s, 2H), 4.60(s, 2H), 4.59(ABq, 2H), 3.79[dd(J=6.9 and 9.6Hz), 1H], 3.66[dd(J=6.9 and 9.6Hz), 1H], 3.59(m, 4H), 3.36(s, 3H), 3.18(m, 1H), 2.13(s, 3H), 1.21[d(J=7.3Hz), 3H] |
| 3-4-(4) | MTM | IR(neat): 1705, 1581, 1453, 1358, 1275(broad), 1069, 1025(cm⁻¹) |
| | | NMR δ (CDCl₃): 7.34(m, 10H), 5.21 s, 2H), 4.62[bd(J=5.0Hz), 2H], 4.48(ABq, 2H), 3.74[dd(J=6.9 and 9.6Hz), 1H], 3.61[dd(J=6.9 and 9.2Hz), 1H], 3.17(m, 1H), 2.14(s, 3H), 2.06(s, 3H), 1.22[d(J=7.3Hz), 3H] |
| 3-4-(5) | Bn | IR(neat): 1698, 1580, 1445, 1352, 1260(broad), 1090, 1020(cm⁻¹) |
| | | NMR δ (CDCl₃): 7.29(m, 15H), 5.17 s, 2H), 4.56(broad s, 2H), 4.36[d (J=2.6Hz), 2H], 3.62(m, 2H), 3.21 (m, 1H), 2.14(s, 3H), 1.21[d(J=7.3Hz), 3H] |
| 3-4-(6) | tBu | IR(neat): 1705, 1580, 1451, 1360, 1270(broad), 1195, 1070(cm⁻¹) |
| | | NMR δ (CDCl₃): 7.35(m, 10H), 5.20 (s, 2H), 4.67(broad s, 2H), 3.65 broad s, 1H), 3.43(broad t, 1H), 3.07 (broad s, 1H), 2.14(s, 3H), 1.19 [d(J=7.3Hz), 3H] |
| 3-4-(7) | Tr | IR(neat): 1698, 1580, 1442, 1358, 1270(broad), 1060, 1021(cm⁻¹) |
| 3-4-(8) | TBMS | IR(neat): 1705, 1592, 1455, 1360, 1255, 1093(cm⁻¹) |

REFERENCE EXAMPLE 3-5

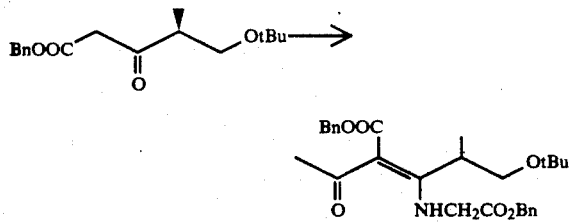

In the same manner as in Reference Example 3-4 but replacing benzylamine by glycine benzyl ester, there was produced benzyl 2-acetyl-3-benzyloxycarbonylmethylamino-4-methyl-5-t-butoxypentenoate.

IR (neat): 1747, 1702, 1588, 1450, 1358, 1190 (cm⁻¹).

REFERENCE EXAMPLE 4-1-(1)

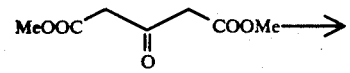

Dimethyl acetonedicarboxylate (50 g; 0.29 mmole) was dissolved in toluene (150 ml), and benzylamine (32.2 g; 0.3 mmole) was added thereto. The resultant mixture was heated under reflux for 30 minutes while elimination of water and then cooled to room temperature. Gaseous ketene was introduced therein. The precipitated crystals were collected by filtration and recrystallized from ethanol to give dimethyl 2-acetyl-3-benzylamino-2-pentenedioate. M.P., 123.5°-124.0° C.

IR (Nujol): 1718, 1685, 1585, 1365, 1092 (cm⁻¹).

REFERENCE EXAMPLE 4-1-(2)

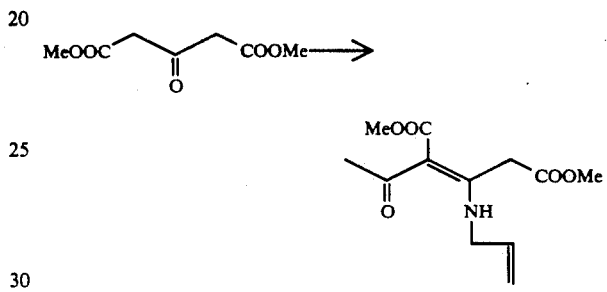

In the same manner as in Reference Example 4-1-(1) but using dimethyl acetonedicarboxylate (10 g; 57.4 mmole) and allylamine (11.5 g; 0.2 mmole), there was produced dimethyl 2-acetyl-3-allylamino-2-pentenedioate. M.P., 91.5°-92.0° C.

REFERENCE EXAMPLE 4-2-(1)

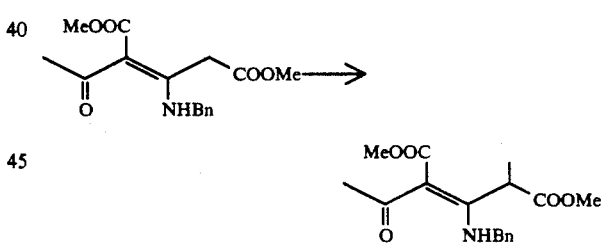

Under nitrogen stream, 60 % sodium hydride (1.68 g; 42 mmole) was added to dry tetrahydrofuran (10 ml), and a solution of dimethyl 2-acetyl-3-benzylamino-2-pentenedioate (6.2 g; 20 mmole) in dry tetrahydrofuran (40 ml) was portionwise added thereto with ice-cooling, followed by stirring at the same temperature for 15 minutes. Methyl iodide (5.68 g; 40 mmole) was added thereto at room temperature, and the resultant mixture was stirred at room temperature for 1 hour and at 40° C. for 1 hour. Water was added to quench the reaction, and the reaction mixture was diluted with ethyl acetate. The organic layer was washed successively with water, dilute hydrochloric acid and an aqueous sodium chloride solution, dried over anhydrous sodium sulfate and concentrated under reduced pressure. The residue was purified by silica gel column chromatography to give dimethyl 2-acetyl-3-benzylamino-4-methyl-2-pentenedioate.

IR (neat): 1735, 1698, 1582, 1427, 1256 (cm⁻¹).

REFERENCE EXAMPLE 4-2-(2)

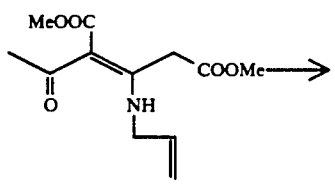

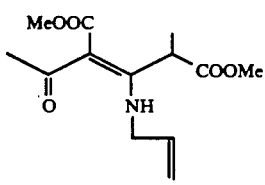

In the same manner as in Reference Example 4-2-(1) but using 60 % sodium hydride (0.8 g; 20 mmole), dimethyl 2-acetyl-3-allylamino-2-pentenedioate (2.55 g; 10 mmole) and methyl iodide (2.84 g; 20 mmole), there was produced dimethyl 2-acetyl-3-allylamino-4-methyl-2-pentenedioate.

IR (neat): 1739, 1700, 1583, 1431, 1262 (cm$^{-1}$).

REFERENCE EXAMPLE 5-1

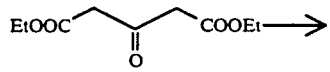

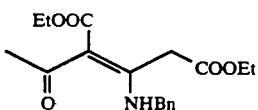

In the same manner as in Reference Example 4-1-(1) but using diethyl acetonedicarboxylate (10.11 g; 50 mmole) and benzylamine (5.57 g; 52 mmole), there was produced diethyl 2-acetyl-3-benzylamino-2-pentenedioate. M.P., 85°–86° C.

REFERENCE EXAMPLE 5-2

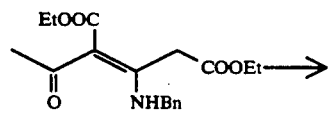

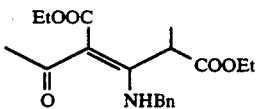

In the same manner as in Reference Example 4-2-(1) but using 60 % sodium hydride (88 mg; 2.2 mmole), diethyl 2-acetyl-3-benzylamino-2-pentenedioate (333 mg; 1 mmole) and methyl iodide (156 mg; 1.1 mmole), there was produced diethyl 2-acetyl-3-benzylamino-4-methyl-2-pentenedioate.

IR (neat): 1730, 1696, 1580, 1438, 1257 (cm$^{-1}$).

REFERENCE EXAMPLE 6-1

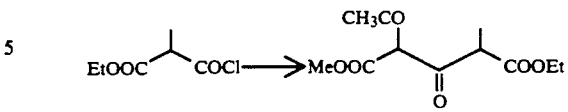

Methyl acetoacetate sodium salt (1.24 g; 9 mmole) prepared from methyl acetoacetate and sodium methoxide was suspended in dry toluene (10 ml), and a solution of ethyl 2-chloroformylpropanoate (1.12 g; 6.8 mmole) in dry toluene (5 ml) was dropwise added thereto at room temperature. The resultant mixture was stirred at the same temperature for 1 hour, and insoluble materials were removed by filtration. The filtrate was concentrated at 40° C. under reduced pressure, and the residue was purified by silica gel column chromatography to give ethyl 3,5-dioxo-4-methoxycarbonyl-2-methylhexanoate.

IR (neat): 1750 (sh), 1730 (sh), 1720, 1570 (broad), 1435 (cm$^{-1}$).

REFERENCE EXAMPLE 6-2

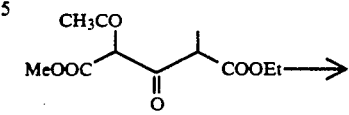

Ethyl 3,5-dioxo-4-methoxycarbonyl-2-methylhexanoate (176 mg; 0.72 mmole) was dissolved in tetrahydrofuran (1.3 ml), and 1.7N aqueous ammonia (0.85 ml) was added thereto at room temperature. The resultant mixture was allowed to stand at the same temperature overnight, followed by removal of tetrahydrofuran under reduced pressure. The reaction mixture was combined with 1N hydrochloric acid (0.7 ml) and an aqueous sodium chloride solution and extracted with ethyl acetate. The organic layer was dried over anhydrous magnesium sulfate and anhydrous sodium sulfate and concentrated under reduced pressure. The residue was purified by silica gel column chromatography to give methyl 4-ethoxycarbonyl-3-oxopentanoate.

IR (neat): 1735, 1720 (sh), 1438, 1322, 1240, 1193 (cm$^{-1}$).

NMR δ (CDCl$_3$) 1.28 [t (J=7.1 Hz), 3H], 1.37 [d (J=7.3 Hz), 3H], 3.63 (m, 2H), 3.74 (s, 3H), 4.20 [q (J=7.1 Hz), 2H].

REFERENCE EXAMPLE 6-3

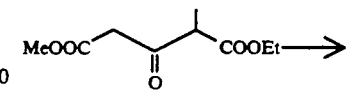

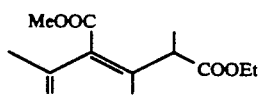

Methyl 4-ethoxycarbonyl-3-oxopentanoate (200 ml; 1.06 mmole) was dissolved in dry methanol (2.5 ml), and benzylamine (386 mg; 3.6 mmole) and molecular sieve 3A (0.3 g) were added thereto. A solution of acetyl chloride (170 mg; 2.17 mmole) in dry methanol (0.9 ml) was added to the resultant mixture, followed by allowing to stand at room temperature for 16 hours. Molecular sieve was removed by filtraton, and the filtrate was diluted with ethyl acetate, washed successively with a saturated sodium bicarbonate solution and water, dried over anhydrous sodium sulfate and concentrated under reduced pressure. The residue was dissolved in toluene (2.5 ml). Gaseous ketene was introduced therein at room temperature. After completion of the reaction, the solvent was removed under reduced pressure, and the residue was purified by silica gel column chromatography to give methyl ethyl 2-acetyl-3-benzylamino-4-methyl-2-pentenedioate.

IR (neat): 1727, 1692, 1575, 1428, 1252 (cm$^{-1}$).

NMR δ (CDCl$_3$): 4.52 (m, 3H), 3.71 (s, 3H), 2.31 (s, 3H), 1.42 [d (J=7.3 Hz), 3H].

REFERENCE EXAMPLE 7-1

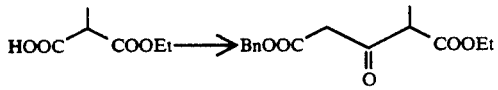

In the same manner as in Reference Example 1-2 but using ethyl 2-carboxypropionate (3.65 g; 25 mmole), 1,1'-carbonyldiimidazole (4.455 g; 27.5 mmole) and malonic acid monobenzyl ester magnesium salt (11.275 g; 27.5 mmole), there was produced benzyl 4-ethoxycarbonyl-3-oxopentanoate.

IR (neat): 1730, 1445, 1370, 1315, 1230, 740, 690 (cm$^{-1}$).

NMR δ (CDCl$_3$) 7.35 (s, 5H), 5.17 (s, 2H), 4.16 [q (J=7.0 Hz), 2H], 3.70 [q (J=7.0 Hz), 1H], 3.67 (s, 2H), 1.35 [d (J=7.0 Hz), 3H)], 1.24 [t (J=7.0 Hz), 3H].

REFERENCE EXAMPLE 7-2-(1)

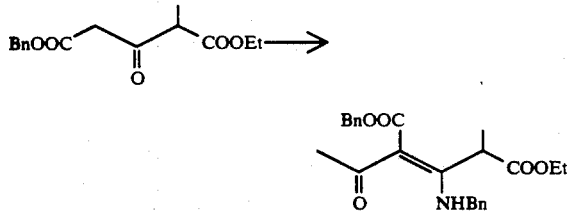

Benzyl 4-ethoxycarbonyl-3-oxopentanoate (695 mg; 2.5 mmole) and benzylamine (535 mg; 5.0 mmole) were dissolved in isopropanol (1.4 ml), and triethylamine hydrochloride (260 mg; 1.875 mmole) and powdery molecular sieve 3A (0.7 g) were added thereto, followed by stirring at 80 to 90° C. for 3 to 4 hours. The reaction mixture was cooled to room temperature, and insoluble materials were collected by filtration and washed with ethyl acetate. The filtrate and the washings were combined together, diluted with ethyl acetate (15 ml) and washed with water two times. The organic layer was dried over anhydrous magnesium sulfate, followed by removal of the solvent under reduced pressure. The residue was thoroughly dried under reduced pressure and dissolved in dry methylene chloride (20 ml). Gaseous ketene was introduced therein at room temperature. After completion of the reaction, the reaction mixture was washed successively with an aqueous sodium bicarbonate solution and an aqueous sodium chloride solution, dried over anhydrous magnesium sulfate and concentrated under reduced pressure. The oily residue was purified by silica gel column chromatography to give ethyl benzyl 2-acetyl-3-benzylamino-4-methyl-2-pentenedioate.

IR (neat): 1733, 1692, 1578, 1450, 1255, 1120, 1085, (cm$^{-1}$).

NMR δ (CDCl$_3$) 7.36 (m, 10H), 5.19 (ABq, 2H), 4.48 (m, 2H), 3.94 (m, 1H), 2.26 (s, 3H), 1.42 [d (J=7.3 Hz), 3H], 1.15 [t (J=7.3 Hz), 3H].

REFERENCE EXAMPLE 7-2-(2)

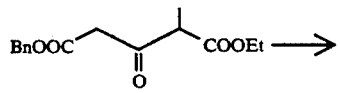

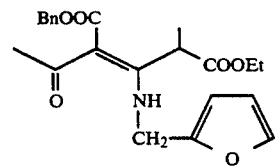

In the same manner as in Reference Example 7-2-(1) but using furfurylamine in place of benzylamine, there was produced ethyl benzyl 2-acetyl-3-furfurylamino-4-methyl-2-pentenedioate.

IR (neat): 1730, 1690, 1580, 1435, 1248, 1115, 1075 (cm$^{-1}$).

NMR δ (CDCl$_3$): 7.36 (m, 5H), 6.32 [dd (J=2.0 and 3.3 Hz), 1H], 6.26 [dd (J=0.7 and 3.3 Hz), 1H], 5.19 (ABq, 2H), 4.43 (m, 2H), 2.24 (s, 3H), 1.46 [d (J=6.9 Hz), H], 1.20 [t (J=7.3 Hz), 3H].

REFERENCE EXAMPLE 7-2-(3)

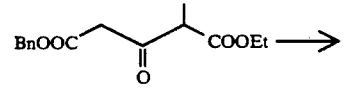

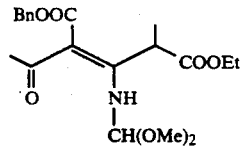

In the same manner as in Reference Example 3-4 but using 2-aminoacetaldehyde dimethyl acetal in place of benzylamine, there was produced ethyl benzyl 2-acetyl-3-dimethoxymethylamino-4-methyl-2-pentenedioate.

IR (neat): 1731, 1692, 1580, 1440, 1358, 1243, 1125, 1070 (cm$^{-1}$).

NMR δ (CDCl$_3$) 7.36 (m, 5H), 5.18 (ABq, 2H), 4.45 [t (J=5.3 Hz), 1H], 3.42 (s, 6H), 2.24 (s, 3H), 1.42 [d (J=7.3 Hz), 3H], 1.22 [t (J=7.3 Hz), 3H].

REFERENCE EXAMPLE 7-2-(4)

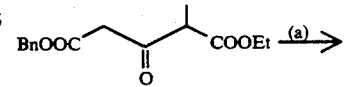

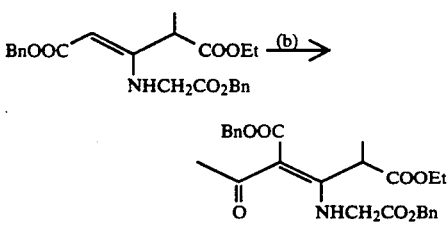

(a) Benzyl 4-ethoxycarbonyl-3-oxopentanoate (278 mg; 1.0 mmole) was dissolved in a mixture of isopropanol (0.4 ml) and benzyl alcohol (0.8 ml), and glycine benzyl ester hydrochloride (605 mg; 3.0 mmole), triethylamine (303 mg; 3.0 mmole) and molecular sieve 3A (0.3 g) were added thereto, followed by allowing it to stand for 2 days. Insoluble materials were removed from the reaction mixture by filtration, and the filtrate was washed with chloroform. After removal of the solvent, the oily residue was purified by silica gel column chromatography to give an acetylenamine.

(b) The acetylenamine as above obtained was dissolved in dry methylene chloride (1 ml), and gaseous ketene was introduced therein. After completion of the reaction, the solvent was removed under reduced pressure, and the residue was purified by silica gel column chromatography to give ethyl benzyl 2-acetyl-3-benzyloxycarbonyl-methylamino-4-methyl-2-pentenedioate.

IR (neat): 1750, 1730, 1682, 1580 (broad), 1452, (broad), 1115, 1042 (cm$^{-1}$).

REFERENCE EXAMPLE 8

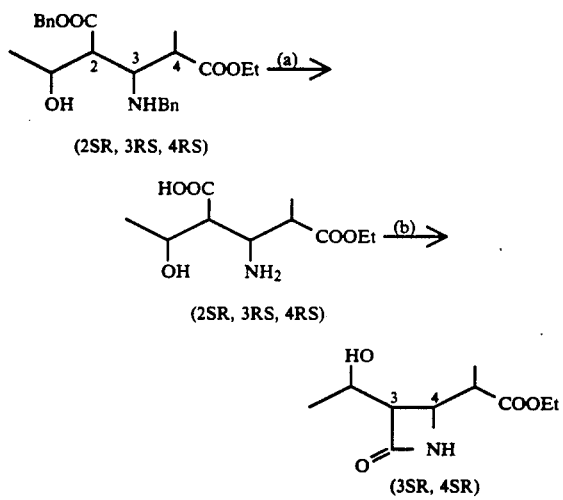

(a) Ethyl benzyl (2SR,3RS,4RS)-2-[1(SR)-hydroxyethyl]-3-benzylamino-4-methylpentanedioate (509 mg) was dissolved in methanol (5 ml), and palladium hydroxide-carbon (102 mg) was added thereto, followed by shaking at room temperature under hydrogen atmosphere (3 to 4 kg/cm$^2$). After consumption of the designed amount of hydrogen, the catalyst was removed by filtration. The filtrate was concentrated under reduced pressure to give (2SR,3RS,4RS)-2-[1(SR)-hydroxyethyl]-3-amino-4-ethoxycarbonylpentanoic acid.

IR (neat): 3350 (broad), 1720, 1620 (sh), 1590 (broad), 1205 (cm$^{-1}$).

(b) The thus obtained (2SR,3RS,4RS)-2-[1(SR)-hydroxyethyl]-3-amino-4-ethoxycarbonylpentanoic acid was suspended in dry acetonitrile (5 ml), and N,N'-dicyclohexylcarbodiimide (266 mg) was added thereto, and the resultant mixture was stirred at room temperature for 10 minutes and at 60° C. for 2 hours. After removal of the solvent under reduced pressure, ethyl acetate (5 ml) was added to the residue, followed by stirring at room temperature. The suspension was allowed to stand at 5° C. for 5 hours, and insoluble materials were collected by filtration and washed with cold ethyl acetate. The filtrate and the washings were combined together and concentrated under reduced pressure. The residue was purified by silica gel column chromatography to give (3SR,4SR)-3-[1(SR)-hydroxyethyl]-4-[1-(RS)-ethoxycarbonylethyl]-2-azetidinone.

IR (neat): 3400 (sh), 3300 (broad), 1760 (sh), 1730 (broad), 1455, 1370, 1180 (cm$^{-1}$).

NMR $\delta$ (CDCl$_3$) 2.65 (m, 1H), 3.06 [dd (J=2.3 and 5.6 Hz), 1H], 3.71 [dd (J=2.3 and 7.3 Hz), 1H].

REFERENCE EXAMPLE 9

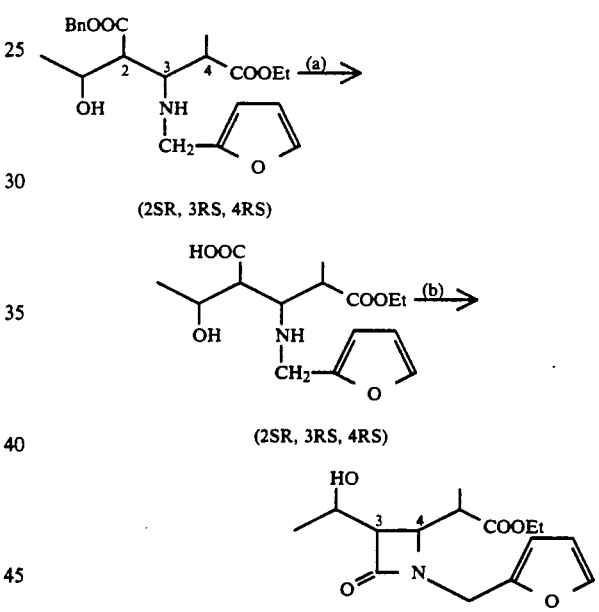

(a) Ethyl benzyl (2SR,3RS,4RS)-2-[1(SR)-hydroxyethyl]-3-furfurylamino-4-pentanedioate (40 mg; 0.1 mmole) was dissolved in ethanol (1 ml), 10 % palladium-carbon (8 mg) was added thereto, and the resultant mixture was subjected to hydrogenation at room temperature under the atmospheric pressure. After completion of the reaction, the catalyst was removed by filtration, and the solvent was distilled off under reduced pressure to give (2SR,3RS,4RS)-2-[1(SR)-hydroxyethyl]-3-furfurylamino-4-ethoxycarbonylpentanoic acid.

IR (neat): 1730, 1705 (sh), 1590, 1380, 1195, 1010, 750 (cm$^{-1}$).

(b) The thus obtained (2SR,3RS,4RS)-2-[1(SR)hydroxyethyl]-3-furfurylamino-4-ethoxycarbonylpentanoic acid (29 mg; 0.1 mmole) was dissolved in dry acetonitrile (2 ml), and after addition of dicyclohexylcarbodiimide (25 mg; 0.12 mmole) at room temperature, the resultant mixture was stirred at 60° to 65° C. for 2.5 hours. The reaction mixture was allowed to stand at room temperature, and insoluble dicyclohexylurea was removed by filtration. The filtrate was concentrated under reduced pressur, and the residue was purified by silica gel column chromatography to give (3SR,4SR)-3-[1(SR)-hydroxyethyl]-4-[1-(RS)-ethoxycarbonyl]ethyl-1-furfuryl-2-azetidinone.

IR (CHCl₃) 3450 (broad), 1740, 1375, 1178, 1050, 1012 (cm⁻¹).

NMR δ (CDCl₃) 7.37 (m, 1H), 6.33 [dd (J=2.0 and 3.3 Hz), 1H], 6.27 [dd (J=0.7 and 3.3 Hz), 1H], 4.42 (ABq, 2H), 4.02 (m, 1H), 3.61 [dd (J=2.3 and 5.3 Hz), 1H], 3.09 (m, 1H), 2.81 (m, 1H), 2.23 [d (J=5.0 Hz), 1H], 1.19 –1.29 (9H).

REFERENCE EXAMPLE 10

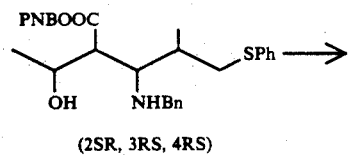

(2SR, 3RS, 4RS)

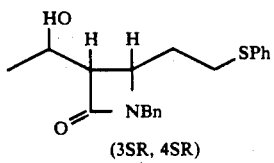

(3SR, 4SR)

p-Nitrobenzyl (2SR,3RS,4RS)-2-[1(SR)-hydroxyethyl]-3-benzylamino-4-methyl-5-phenylthiopentanonate (Ia) (30 mg; 0.059 mmole) was added to conc. hydrochloric acid (2 ml), and the resultant mixture was heated under reflux for 17 hours, followed by removal of hydrochloric acid under reduced pressure. To the residue, acetonitrile was added, and excessive triethylamine was dropwise added thereto for neutralization. After removal of the solvent and excessive trietylamine under reduced pressure, acetonitrile (1 ml), 2,2'-dipyridyl disulfide (26 mg; 0.12 mmole) and triphenylphosphine (31 mg; 0.12 mmole) were added thereto at room temperature, and the resulting mixture was heated under reflux for 5.5 hours. Allowing to stand at room temperature, the solvent was removed under reduced pressure, and the residue was purified by silica gel column chromatography to give (3SR,4SR)-3-[1(SR)-hydroxyethyl]-4-[1-(RS)-methyl2-phenylthio]ethyl-1-benzyl-2-azetidinone.

IR (neat): 3430, 1738, 1578, 1437, 1395, 1375, 1012 (cm⁻¹).

NMR δ (CDCl₃) 7.23 (m, 10H), 4.68 [d (J=15.2 Hz), 1H], 3.93 (m, 1H), 3.78 [d (J=15.2 Hz), 1H], 3.30 [dd (J=2.3 and 5.0 Hz), 1H], 2.50 [dd (J=9.2 and 12.7 Hz), 1H], 1.87 (m, 1H), 1.20 [d (J=6.3 Hz), 3H], 0.97 [d (J=6.6 Hz),3H].

REFERENCE EXAMPLE 11 ·

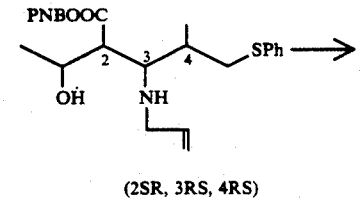

(2SR, 3RS, 4RS)

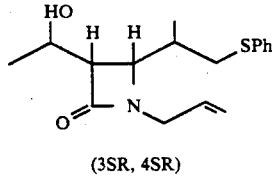

(3SR, 4SR)

In the same manner as in Reference Example 10 but using p-niorobenzyl (2SR,3RS,4RS)-2-[1(SR)-hydroxyethyl]-3-allylamino-4-methyl-5-phenylthiopentanoate (27 mg; 0.06 mmole), there was produced (3SR,4SR)-3-[1(SR)-hydroxyethyl]-4-[1-(RS)-methyl-2-phenylthio]ethyl-1-benzyl-2azetidinone.

IR (neat): 3425, 1740, 1639, 1439, 1398, 1376, 1275, 927 (cm⁻¹).

NMR δ (CDCl₃) 7.34 (m, 5H), 5.70 (m, 1H), 5.21 (m, 2H), 3.55 [dd (J=2.3 and 5.0 Hz), 1H], 3.43 [dd (J=7.3 and 16.8 Hz), 1H], 3.04 [dd (J=4.3 and 12.9 Hz), 1H], 2.87 [dd (J=1.7 and 6.6 Hz), 1H], 2.65 [dd (J=8.9 and 12.9 Hz), 1H], 2.00 (m, 1H), 1.31 [d (J=6.3 Hz), 3H], 1.13 [d (J=6.9 Hz), 3H].

REFERENCE EXAMPLE 12-1

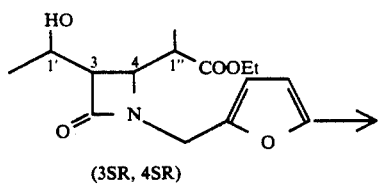

(3SR, 4SR)

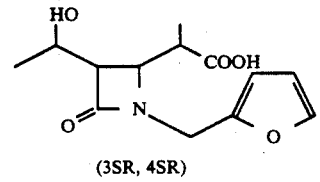

(3SR, 4SR)

(3SR,4SR)-3-[1(SR)-Hydroxyethyl]-4-[1(RS)-ethyl-1-furfuryl-2-azetidinone (30 mg; 0.1 mmole) was dissolved in methanol (0.3 ml), and 0.2 N sodium hydroxide solution (0.5 ml; 0.1 mmole) was dropwise added thereto under ice-cooling. The resultant mixture was stirred at the same temperature for 10 hours. The reaction mixture was diluted with ethyl acetate. The aqueous layer was separated from the organic layer, adjusted to pH 2 with dilute hydrochloric acid and extracted with methyl isobutyl ketone. The extract was washed successively with water and an aqueous sodium chloride solution and dried over anhydrous sodium sulfate. The solvent was removed under reduced pressure to give (3SR,4SR)-3-[1(SR)-hydroxyethyl]-4-[1-(RS)-carboxy]ethyl-1-furfuryl-2-azetidinone. M.P., 125°–127° C.

IR (KBr): 3450, 3370, 1723, 1692 (sh), 1437, 1210 (cm⁻¹).

NMR δ (CD₃OD) 4.42 (ABq, 2H), 4.02 (m, 1H), 3.78 [dd (J=2.3 and 4.6 Hz), 1H], 3.78 (m, 1H), 2.83 (m, 1H), 1.25 [d (J=6.3 Hz), 3H], 1.16 [d (J=7.3 Hz), 3H].

REFERENCE EXAMPLE 12-2

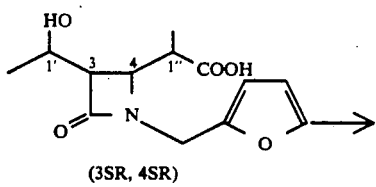

(3SR, 4SR)

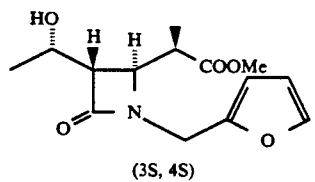

(3S, 4S)

Cinchonidine (20 mg; 0.068 mmole) and 3-(1-hydroxyethyl)-4-(carboxyethyl)-1-furfuryl-2-azetidinone [(3S,4S,1'S,1"R):(3R,4R,1'R,1"S):(3S,4S,1'S,1"S) : (3R,4R,1'R,1"R)=45:45:5:5](20 mg; 0.075 mmole) were dissolved in a mixture of ethyl acetate (1 ml) and isopropanol (0.1 ml) under heating, and the resultant mixture was allowed to stand at room temperature for 12 hours. The precipitated crystals were collected by filtration to give (3S,4S)-3-[1(S)-hydroxy-ethyl]-4-[1(R)-carboxyethyl]-1-furfuryl-2-azetidinone cinchonidine salt (18.5 mg). M.P., 177.5°–178.5° C.

The thus obtained cinchonidine salt was dissolved in 1N hydrochloric acid and extracted with methyl isobutyl ketone. The extract was washed with an aqueous sodium chloride solution, dried over anhydrous sodium sulfate and concentrated under reduced pressure to give (3S,4S)-3-[1(S)-hydroxyethyl]-4-[1-(R)-carboxyethyl]-1-furfuryl-2-azetidinone (9 mg). The substance was then dissolved in a mixture of benzene (0.4 ml) and methanol (1 ml), and a 10 % hexane solution of trimethylsilyldiazomethane (40 mg; 0.035 mmole) was added thereto, followed by stirring at room temperature for 30 minutes. The solvent was removed under reduced pressure, and the residue was purified by silica gel column chromatography to give a mixture mainly containing (3S,4S)-3-[1(S)-hydroxyethyl]-4-[1-(R)-methoxycarbonyl]ethyl-1-furfuryl-2-azetidinone.

HPLC analysis (column, OA-3000; developing solvent, EDC-hexane-ethanol=35:65:4): (3S,4S,1'S,1"R) :(3S,4S,1'S,1"S):(3R,4R,1'R,1"S)=88:10:3.

[α]$_D^{25}$= +24.0° (CHCl$_3$)

IR (neat): 3420 (broad), 1745, 1715, 1365, 1193, 1050, 1000 (cm$^{-1}$).

NMR δ (CDCl$_3$): 7.37 (m, 1H), 6.33 (m, 1H), 6.27 (m, 1H), 4.41 (ABq, 2H), 4.02 (m, 1H), 3.69 (s, 3H), 3.61 [dd (J=2.3 and 5.3 Hz), 1H], 3.09 (m, 1H), 2.82 (m, 1H), 1.27 [d (J=6.3 Hz), 3H], 1.21 [d (J=7.3 Hz), 3H].

Use of quinine in place of cinchonidine can also give optically active (3S,4S)-3-[1(S)-hydroxyethyl]-4-[1(R)-methoxycarbonyl]ethyl-1-furfuryl-2-azetidinone.

REFERENCE EXAMPLE 12-3

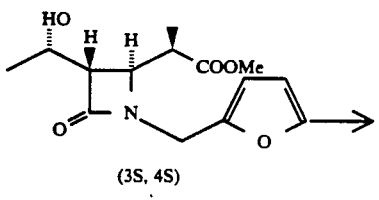

(3S, 4S)

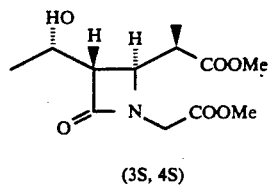

(3S, 4S)

(3S,4S)-3-[1(S)-Hydroxyethyl]-4-[1(R)-methoxycarbonyl]ethyl-1-furfuryl-2-azetidinone as obtained in Reference Example 12-2 (8.0 mg; 0.028 mmole) was dissolved in a mixture of dichloromethane (0.6 ml) and methanol (0.3 ml), and the resulting mixture was cooled to −78° C. Gaseous ozone was introduced therein, and after 30 minutes, the mixture was allowed to stand at room temperature. Triphenylphosphine (8 mg; 0.03 mmole) was added, and stirring was continued for 30 minutes. The solvent was removed under reduced pressure, and the residue was combined with a mixture of benzene (0.75 ml) and methanol (0.25 ml). A 10 % hexane solution of trimethylsilyldiazomethane (100 mg; 0.088 mmole) was further added thereto at room temperature, and the resultant mixture was stirred at the same temperature for 1 hour. After removal of the solvent under reduced pressure, the residue was purified by silica gel column chromatography to give (3S,4S)-3-[1(S)-hydroxyethyl]-[1(R)-methoxycarbonyl]ethyl-1-methoxycarbonylmethyl-2azetidinon IR (CHCl$_3$) 3470 (broad), 1750 (sh), 1732, 1358, 170, 1118 (cm$^{-1}$).

NMR δ (CDCl$_3$) 4.16 (m, 1H), 4.06 (ABq, 2H), 3.99 dd (J=2.6 and 4.6 Hz), 1H], 3.76 (s, 3H), 3.70 (s, 3H), 3.10 [dd (J=2.6 and 6.6 Hz), IH], 2.84 (m, 1H), 1.33 [d (J =6.3 Hz), 3H], 1.25 [d (J=6.9 Hz), 3H].

REFERENCE EXAMPLE 13-1

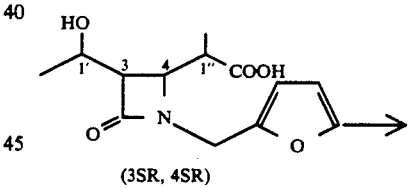

(3SR, 4SR)

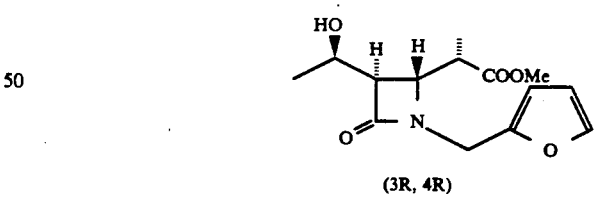

(3R, 4R)

Cinchonine (20 mg; 0.068 mmole) and 3-(1-hydroxyethyl)-4-(carboxyethyl)-1-furfuryl-2-azetidinone [(3S,4S,1'R,1"R):(3R,4R,1'R,1"S):(3S,4S,1'S,1"S) : (3R,4R,1'R,1"R)=45:45:5:5](20 mg; 0.075 mmole) were dissolved in a mixture of ethyl acetate (1 ml) and isopropanol (0.1 ml) under heating, and the resultant mixture was allowed to stand at room temperature for 24 hours. The precipitated crystals were collected by filtration to give (3R,4R)-3-[1(R)-hydroxyethyl]-4-[1(S)-carboxyethyl]-1-furfuryl-2-azetidinone cinchonine salt (17 mg). M.P., 170°– 172° C.

The thus obtained cinchonine salt was treated in the same manner as in Reference Example 12-2 to give a mixture mainly containing (3R,4R)-3-[1(R)-hydroxyethyl]-4-(S)-carboxyethyl]-1-furfuryl-2-azetidinone.

HPLC analysis (column, OA-3000; developing solvent, EDC-hexane-ethanol=35:65:4): (3S,4S,1'S,1''R) (3R,4R,1'R,1''S):(3R,4R,1'R,1''R)=6.5:93:0.5.

[α]$_D^{25}$= −26 4° (CHCl$_3$)

The IR and NMR data of this product were identical to those of the product as obtained in Reference Example 12-2.

REFERENCE EXAMPLE 13-2

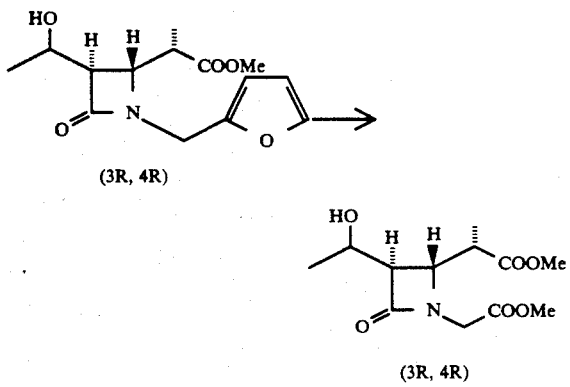

(3R, 4R)

(3R, 4R)

In the same manner as in Reference Example 12-3 but using (3R,4R)-3-[1(R)-Hydroxyethyl]-4-[1-(S)-methoxycarbonyl]ethyl-1-furfuryl-2-azetidinone (8.0 mg) as obtained in Reference Example 13-1, there was produced (3R,4R)-3-(S)-hydroxyethyl]-4-[1-(R)-methoxycarbonyl]ethyl-1-methoxycarbonylmethyl-2-azetidinone.

[α]$_D^{25}$= −11.3° (CHCl$_3$).

The IR and NMR data of this product were identical to those of the product as obtained in Reference Example 12-3.

REFERENCE EXAMPLE 14

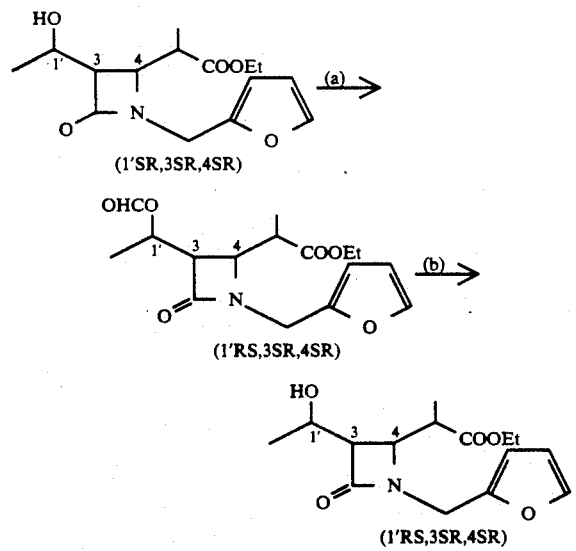

(1'SR,3SR,4SR)

(1'RS,3SR,4SR)

(1'RS,3SR,4SR)

(a) Under nitrogen stream, (3SR,4SR)-3-[1(SR)hydroxyethyl]-4-[1(RS)-ethoxycarbonyl]ethyl-1-furfuryl-2-azetidinone (30 mg; 0.1 mmole) was dissolved in dry tetrahydrofuran (0.3 ml), and triphenylphosphine (31 mg; 0.12 mmole) and 98-100 % formic acid (7 mg; 0.15 mmole) were successively added thereto with ice-cooling, followed by stirring at the same temperature for 5 minutes. Diethyl azodicarboxylate (23 mg; 0.13 mmole) was further added, and the temperature was raised to room temperature, and the resultant mixture was stirred for 21 hours. The solvent was removed by distillation under reduced pressure, and the residue was purified by silica gel column chromatography to give (3SR,4SR)-3-[1(RS)-formyloxyethyl]-4-[1(RS)-ethoxycarbonyl]ethyl-1-furfuryl-2-azetidinone.

IR (CHCl$_3$) 3325, 1738 (sh), 1720, 1395, 1205 (broad), 1170 (cm$^{-1}$).

NMR δ (CDCl$_3$): 7.97 (s, 1H), 7.38 (m, 1H), 6.34 [dd (J=2.0 and 3.3 Hz), 1H], 6.26 [d (J=3.3 Hz), 1H], 5.28 (m, 1H), 4.42 (ABq, 2H), 4.16 [q (J=7.3 Hz), 2H], 3.63 [dd (J=2.0 and 4.6 Hz), 1H], 3.28 [dd (J=2.0 and 7.3 Hz), 1H], 2.85 (m, 1H), 1.38 [d (J=6.3 Hz), 3H], 1.26 [t (J=7.3 Hz), 3H], 1.18 [d (J=7.3 Hz), 3H].

(b) The thus obtained (3SR,4SR)-3-[1(RS)-formyloxyethyl]-4-[1(RS)-ethoxycarbonyl]ethyl-1-furfuryl-2-azetidinone (9.0 mg; 0.029 mmole) was dissolved in methanol (0.2 ml), and anhydrous sodium acetate (12 mg; 0.15 mmole) was added thereto at room temperature, followed by stirring at the same temperature for 2 hours. The reaction mixture was concentrated under reduced pressure, diluted with ethyl acetate and washed succesively with water and an aqueous sodium chloride solution. The organic layer was dried over anhydrous sodium sulfate and concentrated under reduced pressure to give (3SR,4SR)-3-[1(RS)-hydroxyethyl]-4-[1(RS)ethoxycarbonyl]ethyl-1-furfuryl-2-azetidinone.

IR (CHCl$_3$) 3450, 1732, 1370, 1178, 1050, 1005 (cm$^{-1}$).

NMR δ (CDC13) 7.37 (m, 1H), 6.33 [dd (J=2.0 and 3.3 Hz), 1H], 6.26 [d (J=3.3 Hz), 1H], 4.43 (ABq, 2H), 4.15 [q (J=7.3 Hz), 2H], 3.72 [dd (J=2.0 and 5.6 Hz), 1H], 3.05 [dd (J=1.3 and 6.3 Hz), 1H], 2.82 (m, 1H), 2.32 (broad s, 1H), 1.21–1.30 (9H).

REFERENCE EXAMPLE 15

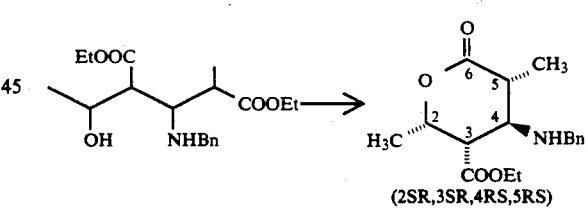

(2SR,3SR,4RS,5RS)

A mixture (105 mg) of the isomers (10a) and (10b) of diethyl 2-[1-hydroxyethyl]-3-benzylamino-4-methylpentanedioate as obtained in Example 14 was dissolved in dry dichloromethane (0.9 ml), and gaseous hydrogen chloride was introduced therein at room temperature for 1 hour, following by stirring for 1.5 hours. The reaction mixture was diluted with diethyl ether (10 ml) and shaken with a saturated sodium bicarbonate solution. The aqueous layer separated from the organic layer was extracted with diethyl ether. The diether ether extract was combined with the organic layer, washed with a saturated sodium chloride solution and dried over magnesium sulfate. After removal of the solvent, the oily residue was purified by thin layer chromatography to give ethyl (2SR,3SR,4RS,5RS)-tetrahydro-2,5-dimethyl-6-oxo-4-benzylamino-2H-pyrane-3-carboxylate.

IR (Nujol): 1730, 1715, 1282, 1198, 1175, 1102 (cm$^{-1}$).

NMR δ (CDCl$_3$): 1.26 [t (J=6.9 Hz), 3H], 1.33 [d (J=6.6 Hz), 3H], 1.45 [d (J=6.6 Hz), 3H], 2.36 [dq (J=8.25 and 6.6 Hz), 1H], 2.77 [dd (J=2.0 and 3.0 Hz), 1H], 3.02 [dd (J=2.0 and 8.25 Hz), 1H], 3.71 [d (J=13.2 Hz), 1H], 3.88 [d (J=13.2 Hz), 1H], 4.18 [dq (J=1.3 and 6.9 Hz), 1H], 4.74 [dq (J=3.0 and 6.6 Hz), 2H].

REFERENCE EXAMPLE 16

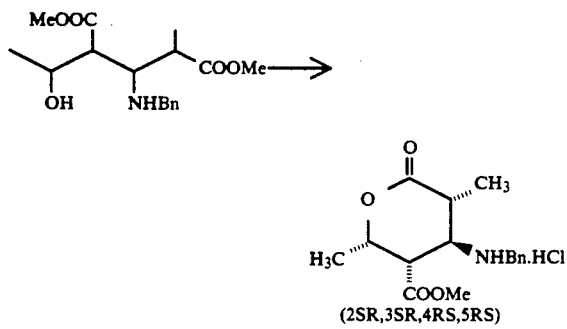

A mixture (2.15 g) of the isomers (4a) and (4b) of dimethyl 2-[1-hydroxyethyl]-3-benzylamino-4-methylpentanedioate as obtained in Example 4 was dissolved in dry dichloromethane (18 ml), and gaseous hydrogen chloride was introduced therein at room temperature for 1 hour, following by stirring for 1 hour. The reaction mixture was concentrated at 30 to 40° C. under reduced pressure, and diethyl ether was added thereto while stirring to give methyl (2SR,3SR,4RS,5RS)-tetrahydro-2,5-dimethyl-6-oxo-4-benzyl-amino-2H-pyrane-3-carboxylate hydrochloride as crystals. M.P., 159.5°-161° C. (decomp.).

REFERENCE EXAMPLE 17

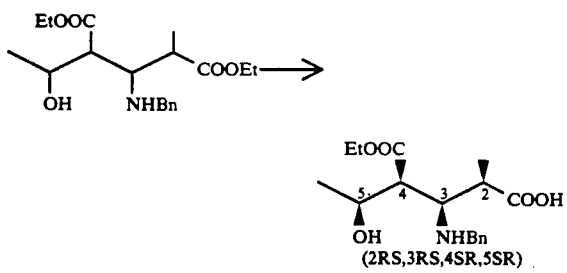

A mixture (140 mg) of the isomers (10a) and (10b) of diethyl 2-(1-hydroxyethyl)-3-benzylamino-4-methylpentanedioate (10a:10b=5:2) as obtained in Example 14 (2.15 g) was dissolved in tetrahydrofuran (4 ml), barium hydroxide (250 mg) and water (2 ml) were added thereto, and the resultant mixture was stirred vigorously at room temperature of 45 minutes. Insoluble materials were collected by filtration and washed with ethanol. The washing and the filtrate were combined together and concentrated under reduced pressure. The residue was subjected to thin layer chromatography, whereupon a new spot was revealed in addition to the spots corresponding to the starting material and the original point. The product as the new spot was collected and fractionally purified to give (2RS,3RS,4SR,5SR)-2-methyl-3-benzylamino-4-ethoxycarbonyl-5-hydroxyhexanoic acid (70 mg).

IR (neat): 1730, 1600, 1455, 1380, 1180, 1105, 1020, 745 (cm$^{-1}$).

NMR δ (CDCl$_3$) 1.23 [d (J=6.6 Hz), 3H], 1.27 [d (J=6.9 Hz), 3H], 1.29 [t (J=7.3 Hz), 3H], 2.61 [dd (J=2.6 and 2.9 Hz), 1H], 2.82 (m, 1H), 3.17 [dd (J=3.0 and 5.6 Hz), 1H], 3.74 [d (J=13.2 Hz), 1H], 3.83 [dq (J=3.0 and 6.6 Hz), IH].

REFERENCE EXAMPLE 18

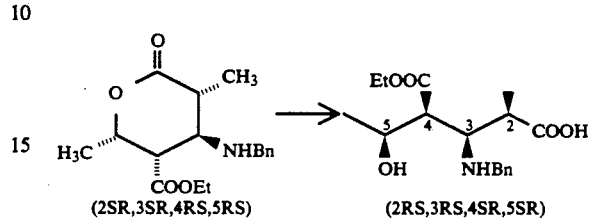

Ethyl ( 2SR,3SR,4RS,5RS)-tetrahydro-2,5-dimethyl-6-oxo-4-benzylamino-2H-pyrane-3-carboxylate (3 mg) and barium hydroxide (7 mg) were dissolved in a mixture of tetrahydrofuran and water (2:1) and stirred vigorously at room temperature for 1 hour. The reaction mixture was treated as in Reference Example 17 to give (2RS,3RS,4SR,5SR)-2-methyl-3-benzylamino-4-ethoxycarbonyl-5-hydroxyhexanoic acid.

The IR and NMR data of this product were identical to those of the product as obtained in Reference Example 17.

REFERENCE EXAMPLE 19

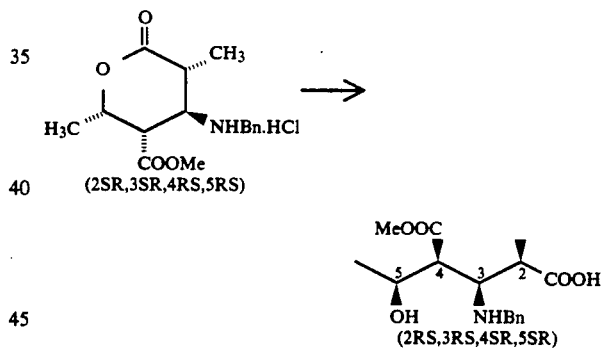

Methyl (2SR,3SR,4RS,5RS)-tetrahydro-2,5-dimethyl-6-oxo-4-benzylamino-2H-pyrane-3-carobxylate hydrochloride (62 mg) was dissolved in tetrahydrofuran (4 ml), barium hydroxide (166 mg) and water (2 ml) were added thereto, and the resultant mixture was vigorously stirred at room temperarture for 1 hour. The reaction mixture was treated as in Reference Example 17 to give (2RS,3RS,4SR,5SR)-2-methyl-3-benzylamino-4-methoxycarbonyl-5-hydroxyhexanoic IR (Nujol): 3300, 1715, 1450, 1400, 1370 (cm$^{-1}$).

REFERENCE EXAMPLE 20

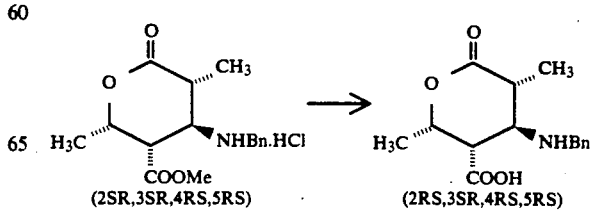

Methyl (2SR,3SR,4RS,5RS)-tetrahydro-2,5-dimethyl-6-oxo-4-benzylamino-2H-pyrane-3-carboxylate hydrochloride (110 mg) was dissolved in conc. hydrochliric acid (0.9 ml), and the resultant mixture was refluxed for 2 hours. After cooling, the reaction mixture was diluted with ethanol and distilled under reduced pressure. The residue was purified by thin layer chromatography to give (2SR,3SR,4RS,5RS)-tetrahydro-2,5-dimethyl-6-oxo-4-benzylamino-2H-pyrane-3-carboxylic acid.

IR (neat): 1722, 1450, 1385, 1205, 1050 (cm$^{-1}$).

REFERENCE EXAMPLE 21

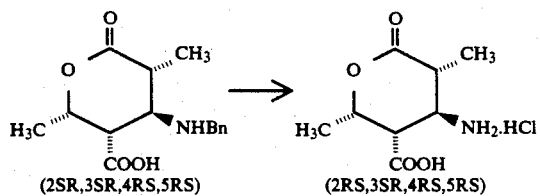

(2SR,3SR,4RS,5RS)-Tetrahydro-2,5-dimethyl-6-oxo-4-benzylamino-2H-pyrane-3-carboxylic acid (100 mg) was dissolved in acetic acid (20 ml), and palladium hydroxidecarbon (prepared by the method as described in J.Am.Chem. Soc., 83, p.4798 (1961)) (20 mg) was added thereto. The resultant mixture was stirred at room temperature under hydrogen pressure of 3-4 kg/cm$^2$ until the designed amount of hydrogen was consumed. The catalyst was collected by filtration and washed with water. The washing and the filtrate were combined together and concentrated at 40° C. under reduced pressure to give (2SR,3SR,4RS,5RS)-tetrahydro2,5-dimethyl-6-oxo-4-amino-2H-pyrane-3-carboxylic acid.

IR (neat): 3400 (broad), 1720, 1385, 1215, 1107 (cm$^{-1}$).

NMR δ (CD$_3$OD) 1.41 [d (J=5.9 Hz), 3H], 1.49 [d (J=6.3 Hz), 3H], 2.95 (m, 1H), 3.69 [dd (J=3.0 and 9.4 Hz), 1H], 5.00 (m, 1H).

REFERENCE EXAMPLE 22

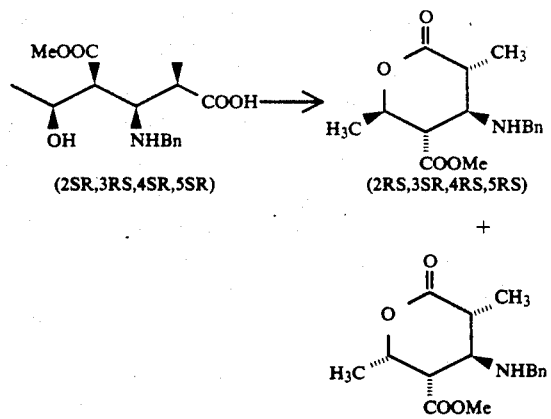

(2RS,3RS,4SR,5SR)-2-Methyl-3-benzylamino-4-methoxycarbonyl-5-hydroxyhexanoic acid (340 mg; 1.1 mmole) and triphenylphosphine (393 mg; 1.5 mmole) were dissolved in dry toluene (6 ml). After addition of triethylamine (151.5 mg; 1.5 mmole), the resultant mixture was cooled to −15° C. Diethyl azodicarboxylate (261 mg; 1.5 mmole) was added thereto, and the mixture was stirred at −10° to −5° C. for 1 hour. The solvent was removed under reduced pressure, and the residue was purified by silica gel column chromatography to give methyl (2RS,3SR,4RS,5RS)-tetrahydro-2,5-dimethyl6-oxo-4-benzylamino-2H-pyrane-3-c (190 mg) and methyl (2SR,3SR,4RS,5RS)-tetrahydro-2,5-dimethyl-6-oxo-4-benzylamino-2H-pyrane-3-carboxylate (55 mg).
(2RS,3SR,4RS,5RS) isomer:

IR (neat): 3300, 1715, 1220, 1058 (cm$^{-1}$).

NMR δ (CDCl$_3$): 1.37 [d (J=6.3 Hz), 3H], 1.42 [d (J=7.3 Hz), 3H], 2.55 (m, 1H), 2.67 [t (J=10.6 Hz), 1H], 3.15 [dd (J=9.6 and 10.6 Hz), 1H], 3.78 (s, 3H), 4.51 [dq (J=10.6 and 7.3 Hz), 1H].

(2SR,3SR,4RS,5RS) isomer:

IR (neat): 1740, 1450, 1390, 1280, 1200, 1172, 1105, 740 (cm$^{-1}$).

NMR δ (CDCl$_3$): 1.34 [d (J=6.6 Hz), 3H], 1.43 [d (J=6.6 Hz), 3H], 2.38 [dq (J=8.25 and 6.6 Hz), 1H], 2.80 dd (J=2.0 and 2.6 Hz), 1H], 3.02 [dd (J=2.0 and 8.25 Hz), 1H], 3.71 [d (J=12.9 Hz), 1H], 3.71 (s, 3H), 3.88 [d (J=12.9 Hz), 1H], 4.74 [dq (J=2.6 and 6.6 Hz), 1H].

What is claimed is:

1. A beta-lactam compound of the formula:

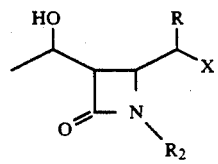

wherein R is a lower alkyl group, R$_2$ is an optionally substituted allyl group of the formula:

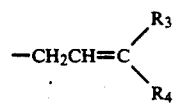

(wherein R$_3$ and R$_4$ are each a hydrogen atom, a lower alkyl group or an aryl group), a beta-hydroxyethyl group in which the hydroxyl group is optionally protected, a formylmethyl group in which the formyl group is optionally protected, a carboxymethyl group in which the carboxyl group is protected carboxyl group, a hydroxymethyl group in which the hydroxyl group is optionally protected or a substituted mercaptomethyl group of the formula:

(wherein R$_5$ is an aryl group or an ar(lower)alkyl group).

2. The beta-lactam compound according to claim 1, wherein R is methyl.

3. A beta-lactam compound of the formula;

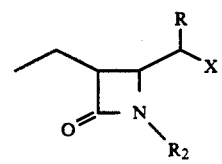

wherein R is a lower alkyl group, R$_2$ is an optionally substituted allyl group of the formula:

—CH₂CH=C(R₃)R₄ (wherein R₃ and R₄ are each a hydrogen atom, a lower alkyl group or an aryl group), a beta-hydroxyethyl group in which the hydroxyl group is optionally protected, a formylmethyl group in which the formyl group is optionally protected, a carboxymethyl group in which the carboxyl group is protected or a 2-furylmethyl group; and X is a hydroxymethyl group in which the hydroxyl group is optionally protected or a substituted mercaptomethyl group of the formula: —CH₂SR₅ )wherein R₅ is an aryl group or an ar(lower)alkyl group).

4. The beta-lactam compound according to claim 1, wherein R is methyl.

5. The beta-lactam compound having the formula;

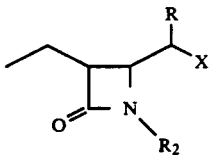

wherein R is methyl, R₂ is 2-furylmethyl and X is carboxyl or protected carboxyl.

* * * * *